US 6,740,731 B2

(12) United States Patent
Bigg et al.

(10) Patent No.: US 6,740,731 B2
(45) Date of Patent: May 25, 2004

(54) DEGRADATION CONTROL OF ENVIRONMENTALLY DEGRADABLE DISPOSABLE MATERIALS

(75) Inventors: Donald M. Bigg, Columbus, OH (US); Richard G. Sinclair, Columbus, OH (US); Edward S. Lipinsky, Worthington, OH (US); John H. Litchfield, Worthington, OH (US); Billy R. Allen, Greenwood, IN (US)

(73) Assignee: Cargill Dow Polymers LLC, Midland, MI (US)

( * ) Notice: Subject to any disclaimer, the term of this patent is extended or adjusted under 35 U.S.C. 154(b) by 0 days.

(21) Appl. No.: 09/782,183

(22) Filed: Feb. 12, 2001

(65) Prior Publication Data

US 2002/0123546 A1 Sep. 5, 2002

Related U.S. Application Data

(63) Continuation of application No. 09/244,324, filed on Feb. 3, 1999, now abandoned, which is a continuation of application No. 07/949,675, filed on Sep. 22, 1992, now abandoned, which is a continuation-in-part of application No. 07/579,000, filed on Sep. 6, 1990, now Pat. No. 5,216,050, and a continuation-in-part of application No. 07/579,005, filed on Sep. 6, 1990, now Pat. No. 5,180,765, and a continuation-in-part of application No. 07/579,460, filed on Sep. 6, 1990, now Pat. No. 5,252,642, and a continuation-in-part of application No. 07/579,465, filed on Sep. 6, 1990, now abandoned, and a continuation-in-part of application No. 07/387,676, filed on Jul. 31, 1989, now abandoned, and a continuation-in-part of application No. 07/387,678, filed on Jul. 31, 1989, now abandoned, and a continuation-in-part of application No. 07/386,844, filed on Jul. 31, 1989, now abandoned, and a continuation-in-part of application No. 07/387,670, filed on Jul. 31, 1989, now abandoned, and a continuation-in-part of application No. 07/317,391, filed on Mar. 1, 1989, now abandoned, which is a continuation-in-part of application No. 07/229,894, filed on Aug. 8, 1988, now abandoned, and a continuation-in-part of application No. 07/229,896, filed on Aug. 8, 1988, now abandoned, and a continuation-in-part of application No. 07/229,939, filed on Aug. 8, 1988, now abandoned.

(51) Int. Cl.$^7$ ............... C08G 63/08; C08K 5/00

(52) U.S. Cl. ............ 528/354; 528/355; 528/357; 528/359; 528/361; 528/363; 528/480; 528/486; 525/411; 525/413; 525/415; 524/306; 524/310; 524/315; 524/317; 524/320; 523/124; 523/125; 523/500; 428/480; 428/364; 428/411.1; 521/98; 521/121; 521/100; 264/212

(58) Field of Search ............... 528/354, 355, 528/357, 359, 361, 363, 480, 486; 525/411, 13, 415; 524/306, 310, 315, 317, 320; 523/124, 125, 500; 428/364, 480, 411.1; 521/98, 121; 264/212

(56) References Cited

U.S. PATENT DOCUMENTS

| | | | | |
|---|---|---|---|---|
| 4,374,938 A | * | 2/1983 | Verhelst et al. | 523/124 |
| 4,428,983 A | * | 1/1984 | Nehen et al. | 427/213.34 |
| 5,085,629 A | * | 2/1992 | Goldberg et al. | 604/8 |
| 5,134,171 A | * | 7/1992 | Hammel et al. | 521/98 |
| 5,180,765 A | * | 1/1993 | Sinclair | 524/306 |
| 5,512,333 A | * | 4/1996 | Suskind | 427/536 |
| 5,539,081 A | * | 7/1996 | Gruber et al. | 528/354 |
| 5,760,118 A | * | 6/1998 | Sinclair et al. | 524/306 |
| 5,854,304 A | * | 12/1998 | Garcia et al. | 523/124 |
| 5,973,024 A | * | 10/1999 | Imashiro et al. | 523/124 |
| 6,245,831 B1 | * | 6/2001 | Tsai et al. | 523/124 |
| 6,313,194 B1 | * | 11/2001 | Yagi et al. | 523/124 |
| 6,482,872 B2 | * | 11/2002 | Downie | 523/124 |
| 2002/0123546 A1 | * | 9/2002 | Bigg et al. | 524/306 |
| 2002/0151618 A1 | * | 10/2002 | Bastioli et al. | 523/124 |
| 2003/0139491 A1 | * | 7/2003 | Denesuk | 523/122 |

* cited by examiner

*Primary Examiner*—P. Hampton-Hightower
(74) *Attorney, Agent, or Firm*—Sheridan Ross P.C.

(57) ABSTRACT

The present invention is directed to a method for reducing waste accumulation by using an environmentally degradable disposable material. The disposable material, which includes a hydroxycarboxylic acid-containing polymer, degrades hydrolytically during operative and disposal stages in a controlled manner such that the disposal degradation rate of the material is accelerated relative to the operative degradation rate of the material.

159 Claims, 1 Drawing Sheet

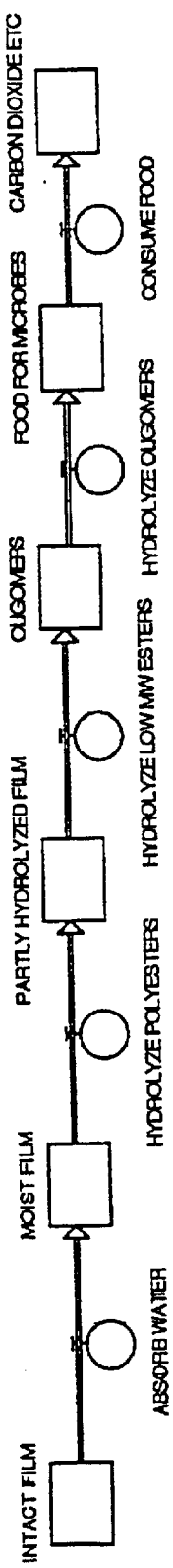
FIGURE 1. MAP OF DEGRADATION OF POLYMER FILM, INCLUDING CHEMICAL REACTIONS AND MORPHOLOGICAL CHANGES OF POLYMER, AND BIOCHEMICAL REACTIONS THAT GENERATE CARBON DIOXIDE

US 6,740,731 B2

DEGRADATION CONTROL OF ENVIRONMENTALLY DEGRADABLE DISPOSABLE MATERIALS

CROSS-REFERENCE TO RELATED APPLICATIONS

The present application is a continuation of U.S. patent application Ser. No. 09/244,324, filed Feb. 3, 1999 now abandoned, entitled "DEGRADATION CONTROL OF ENVIRONMENTALLY DEGRADABLE DISPOSABLE MATERIALS", which is a continuation of U.S. patent application Ser. No. 07/949,675 filed Sep. 22, 1992 now abandoned which is a continuation-in-part of pending U.S. patent application Ser. Nos. 07/579,000 now U.S. Pat. No. 5,216,050, entitled "Blends of Polylactic Acid"; 07/579,005 now U.S. Pat. No. 5,180,765, entitled "Biodegradable Packaging Thermoplastics from Polylactic Acid"; 07/579,460 now U.S. Pat. No. 5,252,642, entitled "Degradable Impact Modified Polylactic Acid"; and 07/579,465 now abandoned, entitled "Biodegradable Replacement of Crystal Polystyrene"; all filed on Sep. 6, 1990; which are continuation-in-parts of U.S. patent application Ser. Nos. 07/387,676; 07/387,678; 07/386,844; and 07/387,670; respectively, all filed on Jul. 31, 1989, and now abandoned; which are continuation-in-parts of U.S. patent application Ser. Nos. 07/229,894, filed Aug. 8, 1988; 07/229,896, filed Aug. 8, 1988; 07/317,391, filed Mar. 1, 1989; and 07/229,939, filed Aug. 8, 1988; respectively, now abandoned; and all of which are incorporated by reference herein in their entirety.

FIELD OF THE INVENTION

The present invention relates to a method for controlling the degradation rate of biodegradable disposable materials which can substitute for common environmentally nondegradable plastics, thereby reducing accumulation of wastes in the environment. The present invention discloses means to provide materials that are relatively stable throughout their useful life but that degrade rapidly upon disposal.

BACKGROUND

There is a need for an environmentally degradable disposable material as a potential replacement for the tremendous amount of conventional plastic materials which, when discarded, do not degrade well. Approximately 60.5 billion pounds of plastic polymers were produced in the United States in 1991, of which approximately 15 billion pounds were one-way, or non-returnable, plastics used in packaging. A significant amount of these plastic materials are discarded and become pollutants that deface the landscape and threaten marine life. At least about one million seabirds and about 100,000 marine mammals die each year as the result of plastic pollutants.

A further problem with the disposal of nondegradable plastics is the concern for dwindling landfill space. It has been estimated that most major cities will have used up available landfills for solid waste disposal during the 1990's. Plastics currently comprise approximately 8 percent of the weight of and about 17 percent of the volume of solid waste.

However, there are good reasons for the use of plastics as, for example, packaging materials. Plastics provide appealing aesthetic qualities in the form of attractive packages which can be quickly fabricated and filled with specified units of products. The packages maintain cleanliness, storage stability, and other desirable qualities such as transparency. Packages made of conventional plastics are known for their low cost of production and chemical stability. This stability, however, leads to the discarded packages remaining in the environment for long periods of time, typically on the order of tens to hundreds of years.

A number of biodegradable polymers have been described, including polymers of some hydroxycarboxylic acids, such as lactic acid, which are attractive because of their biocompatible and thermoplastic nature. Polymers of hydroxycarboxylic acids can be degraded into monomers and small oligomers over time by hydrolysis under most environmental conditions. The resulting monomers and small oligomers are then readily taken up by organisms in the environment and can be aerobically converted to carbon dioxide and water or anaerobically converted to carbon dioxide and methane. Polymers of hydroxycarboxylic acids can also be degraded in the bodies of humans and other animals, a property which has led to the well-documented use of such polymers in the biomedical field as, for example, sutures, implants, and drug delivery devices.

However, the inventors are unaware of anyone having developed or commercialized technology to control the degradation of biodegradable disposable materials in a manner to render such materials useful. That is, a suitable disposable material should be stable throughout its useful life, which spans from when the material was produced through storage and use stages, but should be susceptible to rapid degradation upon disposal. The Kirk-Othmer Encyclopedia of Chemical Technology, 3rd edition, Supplement Volume, Alcohol Fuels to Toxicology, p. 647, 1984, predicts that biodegradable packages are "unlikely to be developed except in very special situations" because biodegradable packages are expensive, deficient in "required" properties, and more difficult to recycle. This article also states that blends of biodegradable polymers with the nondegradable polymers polyethylene, polystyrene, polypropylene, or polyethylene terephthalate are still not biodegradable. Encyclopedia '92, Modern Plastics mid-October 1991 issue, vol. 68, p. 163, also discourages the use of biodegradable polymers, stating that natural polymers "are not yet in large-scale production and are very expensive."

Therefore, a need exists for a cost-effective environmentally degradable disposable material with appropriate properties and desired degradation characteristics.

SUMMARY OF THE INVENTION

The present invention is directed to a method for reducing waste accumulation, such as landfill, fresh water, salt water, or landscape surface waste, which includes the use of an environmentally degradable disposable material. The disposable material, which includes a hydroxycarboxylic acid-containing polymer, degrades hydrolytically during operative and disposal stages in a controlled manner such that the disposal degradation rate of the material is accelerated relative to the operative degradation rate (the operative degradation rate comprising an average of the storage disposal rate and use disposal rate) of the material. Preferably, the operative degradation rate, which can be measured by a change in molecular weight over time, is less than about 50 percent of the disposal degradation rate, more preferably less than about 33 percent, even more preferably less than about 10 percent, and even more preferably less than about 5 percent of the disposal degradation rate. The disposable material is capable of being at least about 98 percent, and preferably about 100 percent, hydrolytically degraded after discard. The material is preferably at least about 98 percent hydrolytically degraded, and more preferably about 100 percent hydrolytically degraded, within about ten years, more preferably within about five years, and even more preferably within about three years. The disposable material can also be degraded by other mechanisms such as biological, chemical, mechanical, photo, and thermal degradation. Disposable materials that are further degraded by biological, preferably microbial, degradation can be degraded essentially to carbon dioxide and water or to carbon dioxide and methane. The disposable material is preferably a film, foam, coating, or molded article, but can also be an extruded article, nonwoven fiber, pellet, powder, laminate, adhesive, etc.

The present invention also includes environmentally degradable disposable materials possessing the above-mentioned characteristics and a method to produce such materials that includes at least one of the following steps: (a) adding at least one activator compound to the material; (b) adding at least one blotting compound to the material; (c) coating the material with at least one coating compound; (d) producing a material comprising a copolymer; (e) adding at least one plasticizer to the material, including varying the amount and type of plasticizer added; (f) modifying the crystallinity of the material; (g) modifying the free volume of the material; (h) modifying the orientation of the material; (i) modifying the molecular weight of the material; (j) modifying the surface area of the material; (k) applying a stress to the material; (l) adding at least one hydrophobic compound to the material; (m) adding at least one end-capping agent to the material; (n) cross-linking the material; and (o) adding at least one source of microbial nutrients to the material.

Preferred hydroxycarboxylic acids of the present invention are α-hydroxycarboxylic acids.

BRIEF DESCRIPTION OF THE FIGURE

FIG. 1 is a schematic depicting the degradation of a film that contains environmentally degradable disposable materials of the present invention.

DETAILED DESCRIPTION OF THE INVENTION

One embodiment of the present invention is an environmentally degradable disposable material which includes a hydroxycarboxylic acid-containing polymer and which degrades hydrolytically during operative and disposal stages in a controlled manner such that the disposal degradation rate of the material is accelerated relative to the operative degradation rate of the material.

An environmentally degradable disposable material of the present invention includes any one-way hydroxycarboxylic acid polymer-containing plastic that does not undergo significant degradation until it is discarded. As used herein, disposable materials of the present invention exist through two stages. The operative stage, during which there is minimal degradation, begins immediately following production of the material and continues until the material is discarded, but excludes any processing performed during this time period. As such, the operative stage includes the time during which the material is stored (sometimes called shelf-life) and used. In one embodiment in which disposable materials of the present invention are packaging materials, the operative stage can also include a packaging stage during which products are packaged using disposable materials (e.g., films or moldings) of the present invention (e.g., when containers composed of disposable materials of the present invention are filled with products such as milk or when products such as meat are packaged by enclosing them in disposable packaging materials of the present invention). However, the operative stage does not include any processing steps, such as when the disposable materials are exposed to harsh conditions, including exposure to heat and moisture (e.g., orientation processing steps or other thermal forming steps).

The disposal stage is the period of time extending from when the disposable material is discarded until the material is at least about 98 percent, and preferably about 100 percent, hydrolytically degraded, as defined hereafter. During the disposal stage, the disposable material, which usually has been discarded in a landfill, in water, or on a landscape surface, can decompose to smaller molecules which are environmentally benign. In one embodiment, the disposal stage also includes the use of other mechanisms to further degrade the disposable materials.

Environmentally degradable disposable materials of the present invention are distinguishable from biodegradable plastics which are used in the body (e.g. sutures, implants, and drug delivery devices), because the latter materials are designed to undergo substantial, and often controlled, degradation during use. In contrast, a disposable material of the present invention begins accelerated degradation during its disposal stage, having exhibited only a minor amount of degradation during its operative stage.

Disposable materials can be produced by a variety of methods, including but not limited to, extruding, molding, coating, calendering, laminating, spraying, and other methods known in the art. Suitable disposable materials of the present invention include, but are not limited to: films; foams; coatings; molded articles, including injection moldings, blown moldings, and thermoformed moldings; extruded articles, including those that are cast or oriented; nonwoven fibers; pellets; powders; laminates; and adhesives. Preferred disposable materials include films, foams, coatings, and molded articles. Examples of disposable materials suitable for use in the present invention include, but are not limited to, packaging materials, such as food product containers (e.g., egg cartons and fast-food containers), beverage containers (e.g., cups, cans, cartons, and six pack containers), and packages containing a variety of other products; utensils; hardware items; hospital supplies, such as sheets, gowns, packages, sample containers, and syringes; bags, such as for trash or cleaning; diaper backings; shipping materials; and coatings, such as for paperboard or other containers.

Disposable materials of the present invention can degrade in a variety of ways, including, but not limited to, hydrolytic, biological, chemical, mechanical, photo, and/or thermal degradation. In accordance with the present invention, disposable materials are preferably degraded hydrolytically, but other degradation methods can be used to further degrade the disposable materials. Preferred methods to further degradation of the materials include biological degradation, such as microbial or biochemical (e.g., enzymatic) action; and thermal induction of degradation, such as exposure of the disposable materials to steam which can trigger degradation by increasing moisture penetration. A more preferred method to further degrade the materials is microbial degradation. Suitable microorganisms to conduct microbial degradation include, but are not limited to, bacteria, yeast and other fungi, algae, protozoa, and mixtures thereof.

As used herein, hydrolytic degradation is the process by which moisture penetrates a disposable material of the present invention and hydrolyzes, for example, ester bonds, thereby breaking down polymers in the material. Without being bound by theory, hydrolytic degradation is thought to proceed through a series of somewhat overlapping steps including: (1) diffusion of water into the material; (2) initial hydrolysis yielding polymers with reduced molecular weight (i.e., conversion of polymers to oligomers); (3) continued loss of molecular weight (i.e., formation of smaller oligomers) and gradual loss of plasticizers incorporated into the material; (4) initial loss of physical properties (e.g., pliability); (5) loss of further properties resulting in an opaque and hazy material; (6) major loss of physical properties, such as tensile strength and form-stability; (7) weight loss; and (8) volume loss, until the material is essentially degraded to monomers or small oligomers. Typically, the obvious loss of physical properties correlates with a reduction in molecular weight of the polymer down to a number average molecular weight of about 50,000 daltons.

An example of a polymer film degradation profile is depicted in FIG. 1, which correlates hydrolysis reactions with physical property changes in the degrading polymer. FIG. 1 shows that the degradation process begins when water, which may obtained from the atmosphere or a liquid, diffuses into (i.e., moistens) the film. In addition, FIG. 1 shows a series of hydrolytic reactions by which polyesters are hydrolyzed into low molecular weight esters, leading to a partly hydrolyzed film, which is then subjected further to hydrolysis into oligomers and finally into monomers and small oligomers that can be consumed by microorganisms. The FIGURE also shows that microbial action can convert monomers and small oligomers to carbon dioxide and either water or methane.

During the operative stage, disposable materials of the present invention are susceptible to moisture diffusion and, possibly, limited hydrolysis. During the disposal stage, as hydrolysis increases, additional carboxyl ends are formed which promote additional hydrolysis both by polarizing ester bonds and by serving as water reservoirs. As such, steps 2 through 5 (discussed herein before) of hydrolytic degradation proceed fairly rapidly, followed by the rest of the degradation process. For example, a disposable material containing uniaxially oriented L- and D,L-lactic acid-containing copolymers shows essentially no molecular weight change when stored in a dry room. However, when the same material is discarded into an environment of about 95° F. and about 95 percent humidity, the molecular weight of the polymers begins to change within about 1 to about 3 weeks; the material becomes cloudy, opaque, and brittle within about 4 weeks. Between about 1 month and about 6 months, the material becomes extremely fragile and degrades to only about 1 percent to about 10 percent of its original molecular weight.

The rate at which an environmental degradable disposable material degrades depends on a variety of factors including, but not limited to: polymer composition, including polymer type, molecular weight, amount and type of plasticizer, amount and type of residual monomer, crystallinity, orientation, intimacy of polymer/plasticizer mixture, and surface-to-volume ratio; as well as the moisture, pH, temperature, and biological activity of the environment into which the material is placed. Degradation rates can be measured using a variety of short- or long-term tests including, but not limited to, environmental chamber tests in which the temperature and humidity of the environment can be manipulated, boiling water tests, seawater tests, microbiologically active sewage sludge tests (such as the aerobic and anaerobic tests recommended by ASTM in the 1992 Annual Book of ASTM Standards, volume 08.03, Plastics (III): D3100-latest, pages 815–822), and composting tests that simulate soil degradation. An advantage of environmental chamber tests is that the conditions are controlled and that degradation rates of disposable materials can be evaluated by accelerated short-term testing under which materials are exposed to harsh conditions. For example, when certain of the disposable materials of the present invention are subjected to conditions in which the temperature is about 95° F. and the relative humidity is about 95 percent, the disposable materials typically degrade at about the same rate as the materials degrade in seawater in the summer, about 16 times as rapidly as the materials degrade in seawater in winter, about 2 to about 8 times as rapidly as materials degrade on a landfill, about 10 times as rapidly as the material degrades in a compost bed, and about 4 to about 100 times as rapidly as materials degrade when buried in a landfill, depending on the moisture content and microbial activity in the landfill.

The rate at which the material is degraded, i.e., the degradation rate, can be monitored by a variety of methods including changes in molecular weight, moisture penetration, stiffness, strength, hardness, weight, volume, shape, transparency, crystallinity, and glass transition temperature (Tg) of the disposable material. Preferably, the degradation rate is monitored by molecular weight changes or moisture penetration analyses of the disposable material. More preferably, the degradation rate is measured by monitoring changes in the average molecular weight (MW) of the polymers over time, using the formula:

$$(MW_{t2} - MW_{t1})/(t_2 - t_1),$$

wherein $MW_{t1}$ is the average molecular weight at a first time point $t_1$ and $MW_{t2}$ is the average molecular weight of the material at a second time point $t_2$. Molecular weight changes can be measured using a gel permeation chromatography device in which the molecular weight of the unknown is compared with polymer standards of known molecular weights. When the molecular weight becomes quite low (i.e., below about 2,000 daltons), it is preferable to use high performance liquid chromatography to measure molecular weight changes.

Moisture penetration can be measured using the Karl Fischer method which is based on a pyridine reaction that can detect moisture at less than 100 ppm.

A preferred disposable material of the present invention is capable of being at least about 98 percent, and preferably about 100 percent, hydrolytically degraded after discard. As used herein, the term "about 100 percent hydrolytically degraded" means that, after being used and thrown away, the material can be degraded essentially to monomers and small oligomers that can be metabolized by microorganisms. (Microorganisms typically can consume hydroxycarboxylic acid-containing oligomers with molecular weights of up to about 1000 daltons, and preferably up to about 600 daltons, depending on the chemical and physical characteristics of the oligomer.) Preferably, disposable materials of the present invention are at least about 98 percent, and more preferably about 100 percent, hydrolytically degraded within about ten years after discard, more preferably within about five years after discard, and even more preferably within about three years after discard. Such time periods are preferable to the 500 to 1000 years that can be required for essentially nondegradable plastics now in use to break down. In addition, many such plastics contain environmentally toxic compounds in their formulation, such as ultraviolet light absorbers and heat stabilizers.

Exposure of the hydrolytically degraded material to microbial action leads to further degradation which can proceed until the microorganisms have converted the material essentially to carbon dioxide and either water or methane, depending on whether the environment is aerobic or anaerobic. As used herein, conversion of disposable materials of the present invention essentially to carbon dioxide and either water or methane refers to the ability of the microorganisms to either assimilate the degraded disposable material and/or to convert the disposable material to carbon dioxide and either water or methane, such that less than about 50 percent, and preferably less than about 1 percent of the original disposable material remains.

In accordance with the present invention, disposable materials of the present invention degrade in a "controlled manner", which refers to the material's ability to degrade more rapidly after having been discarded, or thrown away, than before; i.e., the material's disposal degradation rate is accelerated relative to the material's operative degradation rate. As used herein, an "operative degradation rate" is the average rate at which disposable materials of the present invention degrade during the time period spanning from the end of their production to the time at which they are discarded. As such, an operative degradation rate is influenced by the rate that a disposable material degrades during storage as well as during use (e.g., when items are being removed from a package or container, or when utensils are being used). Thus, the operative degradation rate comprises the average of the storage degradation rate and the use degradation rate. The operative degradation rate does not include any processing steps that the disposable material might undergo during this stage, such as formation into a package, for example. Preferably, operative degradation rates are low and, as discussed above, are the result of moisture diffusion potentially leading to limited hydrolysis. It is within the scope of the present invention that the operative stage may consist of more than one storage or use stage, in which case the operative degradation rate is determined by taking the average of the degradation rates of each stage. Degradation during processing is not taken into account.

As used herein, a "disposal degradation rate" refers to the rate at which a disposable material of the present invention degrades after the material is discarded. Preferably the disposal degradation rate is measured by determining the change in molecular weight of the disposable material during the disposal time period, which spans from the time the disposable material was discarded until the material is substantially degraded. It is desirable that disposable materials of the present invention degrade faster than nondegradable disposable materials and rapidly enough to avoid significant accumulation of discarded materials. In addition, the disposal degradation rate of disposable materials of the present invention is accelerated relative to the operative degradation rate of the disposable materials. That is, the average operative degradation rate, as measured by a decrease in the average molecular weight over time as described above, is less than about 50 percent of the disposal degradation rate, preferably less than about 33 percent, more preferably less than about 10 percent, and even more preferably less than about 5 percent of the disposal degradation rate. Preferably, the disposal degradation rate will be such that there is no appreciable net accumulation of waste at a disposal site.

One embodiment of the present invention is an environmentally degradable disposable material that includes a hydroxycarboxylic acid-containing polymer and that degrades hydrolytically during an operative stage and during a disposal stage in a controlled manner such that the disposal degradation rate of the material is accelerated relative to the operative degradation rate of the material. As used herein, a "hydroxycarboxylic acid-containing polymer" is a polymer that contains at least one type of hydroxycarboxylic acid. The polymer may also contain other materials, including those described in greater detail hereinafter. Preferred polymers are essentially non-toxic, odor-free, biocompatible, and biodegradable. A hydroxycarboxylic acid polymer can be produced by a number of methods including polymerization of: at least one type of hydroxycarboxylic acid; at least one type of cyclic ester of at least one hydroxycarboxylic acid; at least one type of polymer block, including an oligomer block, containing at least one type of hydroxycarboxylic acid or cyclic ester; and mixtures thereof. Polymers of the present invention may be copolymers of hydroxycarboxylic acids, cyclic esters, oligomers, or mixtures thereof. Polymers of the present invention can include other monomers or oligomers, including those that form nondegradable plastics. When copolymerized with hydroxycarboxylic acids, the "nondegradable" portion of the resulting material may, in fact, become degradable by virtue of shorter repeating lengths of the nondegradable portion. Disposable materials of the present invention can include internal or external plasticizers.

As used herein, a hydroxycarboxylic acid includes all of its derivatives that can form polyester linkages in whole or in part, such as esters, salts, and amides thereof. Preferred hydroxycarboxylic acids of the present invention are α-hydroxycarboxylic acids, but other hydroxycarboxylic acids in which the hydroxyl group is attached to a different carbon, such as, but not limited to, the beta-, gamma-, delta-, epsilon-, and/or omega-carbon, can also be used. Suitable α-hydroxycarboxylic acids include lactic acid, glycolic acid, tartaric acid, malic acid, mandelic acid, benzylic acid, hydroxy-valeric acid, 1-hydroxy-1-cyclo-hexane carboxylic acid, 2-hydroxy-2-(2-tetrahydrofuranyl) ethanoic acid, 2-hydroxy-2-(2-furanyl) ethanoic acid, 2-hydroxy-2-phenylpropionic acid, 2-hydroxy-2-methylpropionic acid, 2-hydroxy-2-methylbutanoic acid, 2-hydroxy-2-ethylhexylcarboxylic acid, α-hydroxybutyric acid, α-hydroxyisobutyric acid, α-hydroxypentanoic acid, α-hydroxyhexanoic acid, α-hydroxyheptanoic acid, α-hydroxyoctanoic acid, α-hydroxynonanoic acid, α-hydroxydecanoic acid, α-hydroxydodecanoic acid, α-hydroxymyristic acid, α-hydroxypalmitic acid, α-hydroxystearic acid, α-hydroxyarachidic acid, α-hydroxybehenic acid, α-hydroxylignoceric acid, α-hydroxycerotic acid, α-hydroxyoleic acid, α-hydroxylinoleic acid, α-hydroxylinolenic acid, α-hydroxyarachidonic acid, other α-hydroxycarboxylic acids having a carbon chain with an even number of carbon atoms, and mixtures thereof. Also suitable are α-hydroxycarboxylic acids with a carbon chain containing an odd number of carbon atoms. Examples include, but are not limited to, α-hydroxypelargonic acid, α-hydroxyundecanonic acid, α-hydroxytridecanoic acid, α-hydroxypentadecanonic acid, α-hydroxyheptadecanoic acid, and α-hydroxynonadecanoic acid. Preferred α-hydroxycarboxylic acids include lactic acid, glycolic acid, tartaric acid, malic acid, mandelic acid, benzylic acid, valeric acid, α-hydroxybutyric acid, α-hydroxyoctanoic acid, α-hydroxystearic acid, and mixtures thereof. More preferred α-hydroxycarboxylic acids include lactic acid, glycolic acid, and mixtures thereof. Other preferred embodiments include lactones, such as caprolactone; aliphatic esters of glycols and dicarboxylic acids; and mixtures thereof.

In a preferred embodiment, disposable materials of the present invention include polylactic acid disposable materials (including polylactide disposable materials), polyglycolic acid disposable materials (including polyglycolide disposable materials), substituted polyglycolic acid disposable materials, caprolactone polymer disposable materials, valerolactone polymer disposable materials, and copolymers of two or more of these types.

In accordance with one embodiment of the present invention, the hydrolytic degradation rate of an environmentally degradable disposable material of the present invention can be controlled by a method which includes at least one of the following steps: (a) adding at least one activator compound to the material that accelerates degradation; (b) adding at least one blotting compound to the material that absorbs water or other hydrolytic degradation products; (c) coating the material with at least one coating compound; (d) producing a material comprising a copolymer; (e) adding at least one plasticizer to the material, including varying the amount and type of plasticizer added; (f) modifying the crystallinity, free volume, orientation, molecular weight, and/or surface area of the material; (g) applying a stress to the material; (h) adding at least one hydrophobic compound to the material; (i) adding at least one end-capping agent to the material; and (j) cross-linking the material. If the material is further degraded by microbial action, at least one source of nutrients can be added to the material in order to augment microbial degradation. According to the scope of the present invention, one of the aforementioned steps can produce the desired disposable material; however a combination of more than one of the steps can also be used to produce desired disposable materials. This method is particularly useful in commercial production, and especially large-scale commercial production, of environmentally degradable disposable materials of the present invention.

One embodiment of the present invention is the use of at least one activator compound that promotes degradation to modify and/or control the rate at which disposable materials degrade such that the disposal degradation rate is accelerated relative to the operative degradation rate. Suitable activator compounds include, but are not limited to, acidic compounds, basic compounds that generate hydroxyl ions when exposed to water, moisture-containing compounds, and water. Although it is known that acids, bases, and water can promote degradation of hydroxycarboxylic acid-containing polymers, the inventors are unaware of the incorporation of an activator compound into a disposable material such that when the activator compound is released, it promotes degradation of the disposable material. This property enables a disposable material having activator compounds to demonstrate an accelerated disposal degradation rate.

Acidic activator compounds are thought to promote hydroxycarboxylic acid polymer degradation because the acids not only can polarize ester bonds but they also attract water molecules, both of which lead to accelerated hydrolysis. A preferred acidic activator compound is a strong acid which has suitable melting and boiling points such that the acid will not volatilize during polymerization. Examples of such acidic activator compounds include fumaric acid, succinic acid, tartaric acid, malic acid, adipic acid, citric acid, glutamic acid, methane sulfonic acid, phosphoric acid, polyphosphoric acid, lactic acid oligomers; including acidic salts, hydrated forms, and easily hydrolyzed derivatives thereof; and mixtures thereof. A more preferred acidic activator compound is fumaric acid which has a melting point of 286° C. and which is approved for food use.

Basic activator compounds are thought to promote hydroxycarboxylic acid polymer degradation because the hydroxyl groups can interact with the polymer to promote hydrolysis, thereby reducing polymer molecular weight and crystallinity. Suitable basic activator compounds include, but are not limited to, sodium bicarbonate, sodium carbonate, potassium bicarbonate, potassium carbonate, calcium hydroxide, ammonium borate, and mixtures thereof. A preferred basic activator compound is sodium bicarbonate.

Water is directly responsible for the hydrolysis of hydroxycarboxylic acid-containing polymers. As such, it is a preferred activator compound. However, it is also possible to use as activator compounds moisture sources (i.e., moisture-containing compounds) that provide water. Suitable moisture-containing activator compounds include, but are not limited to, amylose, other starch-based hydrophilic polymers, cellulose-based hydrophilic polymers, hydrates of inorganic acids or salts thereof, and hydrates of organic acids or salts thereof. Water and moisture sources are advantageous because they can initiate the disposable material degradation process even in an environment that has very little water, such as a dry landfill. In one embodiment, a moisture source such as amylose can provide water to begin degradation of polylactic acid. As polylactic acid degradation leads to acid formation, the acid can promote degradation of the moisture source and of the hydroxycarboxylic acid polymer.

Activator compounds of the present invention can be incorporated directly into a disposable material or coated onto a disposable material. Preferably, activator compounds are microencapsulated in a capsule consisting of a material that retains the activator compound until the capsule is disrupted as the result of, for example, abrasion, mechanical pressure, heat, exposure to acid, or exposure to water, as could be found at a disposal site. Disruption of the capsule may be instantaneous or gradual. If a transparent disposable material is desired, the size of a capsule should be less than about 1 micron. For foam or other nontransparent disposable materials, a wider range of capsule sizes is acceptable, for example from about 1 micron to about 50 microns. Preferred capsular formulations include hydroxyacid-containing polymers such as polylactides and polylactic acids; amyloses; ethyl cellulose, polyethylene terephthalate, aliphatic polyesters, and cellulose acetate butyrate. More preferred capsule materials include cellulose acetate butyrate, polylactides, and polyethylene terephthalate.

Disposable materials of the present invention can be blended with activator compounds, including microencapsulated activator compounds. Preferably, the disposable materials are coated or laminated with films that contain microencapsulated activator formulations of the present invention. As such, the microencapsulated activator compounds are more likely to be exposed to environmental impact, such as abrasion, pressure, heat, water, or acid that will trigger release of the activator compounds and accelerate disposable material degradation during the disposal stage.

Another embodiment of the present invention is the use of at least one blotting compound to modify and/or control the rate at which disposable materials degrade such that the disposal degradation rate is accelerated relative to the operative degradation rate. Blotting compounds are compounds that attract and absorb substances that promote degradation, such as moisture and degradation products (e.g., acidic groups). As such, blotting compounds can retard the rate at which disposable materials degrade. However, once the blotting compounds are saturated, the degradation rate will accelerate. Use of an appropriate amount of a blotting compound allows for blotting compound saturation to occur soon after the beginning of the disposal stage. As such, use of an appropriate amount of a blotting compound leads to an accelerated disposal degradation rate relative to the operative degradation rate. Blotting compounds are particularly useful to stabilize disposable materials during processing stages, such as packaging manufacture, when the materials are exposed to high temperatures and/or water. Preferred blotting compounds are essentially not volatile at the temperatures at which polymer formation or packaging occurs. Blotting compounds can also be used to absorb moisture into the disposable material from the environment, such as rainfall in a landfill.

Suitable blotting compounds include, but are not limited to, water grabbers, alkaline compounds capable of neutralizing acid, dry mineral fillers, and mixtures thereof. Suitable water grabbers include dry silica, talc, clays, calcium sulfate, calcium chloride, sodium sulfate, carbodiimides, and mixtures thereof. Suitable alkaline blotting compounds include sodium bicarbonate, sodium acetate, sodium phosphate, and mixtures thereof. Preferred blotting compounds include dry silica gel and calcium sulfate. Blotting compounds can be incorporated directly into the disposable materials or can be microencapsulated in capsules that degrade in the presence of water and acid. For example, since soluble alkaline blotting compounds may actually promote polymer degradation if they are present in the disposable material in free form, such compounds can be incorporated into the disposable material as coated solids which solubilize in the presence of acid or be microencapsulated in a capsule that is susceptible to acid and/or water degradation, so that the blotting compound is released at a rate effective to promote neutralization of the acid. Suitable capsular formulations include hydroxyacid-containing polymers such as polylactides and polylactic acids; amyloses; ethyl cellulose, polyethylene terephthalate, aliphatic polyesters, and cellulose acetate butyrate. Blotting compounds can also be used to stabilize or heal polymers because they can remove water formed during an esterification reaction.

Yet another embodiment of the present invention is to produce a disposable material which is coated with at least one coating compound capable of retarding degradation in such a manner as to modify and/or control the rate at which the disposable material degrades such that the disposal degradation rate is accelerated relative to the operative degradation rate. The coating compound can be applied to the surface or can be mixed with the polymer and bloom (i.e., migrate) to the surface. Other examples of coating processes include, but are not limited to: surface halogenation in which small amounts of fluorine gas and a light catalyst can modify the surface of the disposable material by increasing the contact angle; and plasma polymerization, in which a hydroxycarboxylic acid monomer is exposed to an ionizing field in order to apply a thin surface layer of highly cross-linked material to a disposable material.

A coating compound of the present invention should be compatible with the hydroxycarboxylic acid-containing polymer it is to coat. The coating, which is obtained by coating a disposable material with the coating compound, is preferably prone to abrasion so that it can protect the disposable material during the operative stage, but will still be penetrable to moisture during the disposal stage. Also preferred is a coating that has a high contact angle when the objective is to delay the onset of hydrolytic degradation. A coating with a high contact angle (e.g., at least about 90 degrees) is hydrophobic; it causes water and other hydrophilic substances to bead on the surface, thereby reducing penetration of the disposable material by such substances.

As described above, a particularly preferred coating is one that is prone to abrasion and hydrophobic. Suitable coating compounds include polyvinyl chloride, polyvinylidine chloride, nitrocellulose, polylactic acid, polylactide, polytetramethyl glycolide, polyurethanes, aliphatic polyamides, and polyethylene terephthalate. Preferred coating compounds are poly(L-lactide) and polytetramethyl glycolide.

The coating can be multiple plies or laminates. For example, a less plasticized polymer layer may coat a more plasticized polymer layer. In addition, a more amorphous D,L-polylactic acid can be coated with a more moisture-resistant L-polylactic acid coating. As a further example, a coating can include several layers: one of which is a moisture barrier, one of which is a gas barrier, and one of which is abrasion prone. The layers can be held together with adhesives that contain activators or inhibitors of degradation.

It is within the scope of the present invention to produce a package on which the label of the package is imprinted into the coat of the disposable material. Rapid degradation of the coat, in accordance with the present invention, soon after the package has been disposed, thereby leads to rapid label disintegration.

Yet another embodiment of the present invention is a disposable material that contains at least one copolymer in order to modify and/or control the rate at which disposable materials degrade such that the disposal degradation rate is accelerated relative to the operative degradation rate. Disposable materials of the present invention containing at least one secondary material, such as an additional monomer, polymer block, or polymer, can have very different degradation properties from those of a homopolymer. For example, as the concentration of a secondary material (e.g., monomer, polymer block, or polymer) increases, the crystallinity of the resultant disposable material typically decreases compared to the original homopolymer. For example, polymers with increased amounts of D,L-lactide per amount of L-lactide are more susceptible to degradation than a L-lactide polymer since the copolymer composition is less crystalline. As used herein, D,L-lactide includes both isomers of racemic lactide, the meso isomer of lactide, and/or mixtures thereof. In addition, the resultant disposable material may be, for example, more or less hydrophobic, depending on the nature of the secondary material. For example, block copolymers with polyethylene terephthalate polymer blocks interspersed with polylactic acid polymer blocks increase the hydrophobicity of the resulting polymer, thereby decreasing its degradation rate compared to that of polylactic acid. Copolymers of the present invention have from about 3 percent to about 50 percent of a secondary material, and preferably at least about 10 percent of the secondary material. Methods to produce copolymers are described, for example, in co-pending U.S. patent application Ser. No. 07/579,005.

Copolymers can be produced by polymerizing at least two monomers together. Suitable monomers include, but are not limited to, hydroxycarboxylic acids and cyclic esters thereof, cyclic carbonates, dicarboxylic acids, anhydrides, diisocyanates, glycols, oligomeric polyalkylene adipates, and mixtures thereof. Preferred monomers include cyclic esters of hydroxycarboxylic acids, dilactones, cyclic carbonates, and mixtures thereof. More preferred monomers include L-lactide, D-lactide, D,L-lactide, glycolide, 2-methyl glycolide, tetramethyl glycolide, dioxanone, caprolactone, ethylene carbonate, propylene carbonate, and mixtures thereof.

Block copolymers can also be formed by mixing at least two polymer blocks (including oligomer blocks) together, under conditions such that the polymer blocks are joined to form a block copolymer. Suitable polymer blocks include, but are not limited to, polymers that will enhance degradation, such as hydroxycarboxylic acid polymers, polymers of cyclic esters of hydroxycarboxylic acids, alkyl ester polymers, alkylene carbonate polymers, cyclic carbonate polymers, and polyethylene glycols, as well as polymers that retard degradation, such as polyethylene terephthalates, phthalate esters, polyethylenes, polystyrenes, polyvinyl chlorides, and polypropylenes. Mixtures of such polymer blocks can also be used. Preferred polymer blocks include α-hydroxycarboxylic acid polymers, polymers of cyclic esters of α-hydroxycarboxylic acids, lactone polymers, dilactone polymers, and cyclic carbonate polymers, and mixtures thereof. More preferred polymer blocks include lactic acid polymers, glycolic acid polymers, L-lactide polymers, D-lactide polymers, D,L-lactide polymers, glycolide polymers, polyethylene terephthalates, adipic acid ethylene-glycol polymers, epsilon-caprolactone polymers, delta-valerolactone polymers, and mixtures thereof. Preferably, hydrophobic polymer blocks contain from about 5 to about 50 hydrophobic monomer units. More preferably, hydrophobic polymer blocks contain from about 5 to about 10 hydrophobic monomer units. Hydrophilic polymer blocks can contain from about 5 to about 500 hydrophilic monomer units.

In addition, copolymers can be produced by combining polymer blocks, or oligomers, and monomers. For example, a copolymer can be produced that consists of a polymer which is difficult to degrade interspersed every about 5 to about 20 units with at least one hydroxycarboxylic acid unit. For example, a copolymer containing about 10 polyethylene terephthalate units per lactic acid unit can degrade hydrolytically to a size (i.e., polyethylene terephthalate decamers) that is degradable by microorganisms.

It is within the scope of this embodiment that at least two homopolymers or copolymers can be mixed together to produce a polymer blend for a disposable material with improved degradation characteristics. For example, a hydrophilic polymer can be mixed with a hydrophobic polymer to produce a physical blend that is more hydrophobic than the original hydrophilic polymer and less hydrophobic than the original hydrophobic polymer. Suitable hydrophilic polymers include, but are not limited to, polylactic acid, polyacrylic acid, polyvinyl pyrrolidone, polyvinyl alcohol, polyvinyl acetate, polyethylene glycol, polypropylene glycol, maleic anhydride copolymers, polyanhydrides, polyureas, and mixtures thereof. Suitable hydrophobic polymers include, but are not limited to polyethylene, polystyrene, polyvinyl chloride, polypropylene, acrylonitrile polymers, styrene-butadiene copolymers, polyisoprene, polyalkenoic acids, and mixtures thereof. Intermediate hydrophilic polymers include aliphatic polyamides, polyurethanes, polyalkylene carbonates, and mixtures thereof.

It is also within the scope of this embodiment that copolymers of the present invention can form interpenetrating networks or composites such that the polymers can be intimately dispersed or even covalently attached. For example, a very hydrophobic monomer can be polymerized in the presence of a preformed hydrophilic polymer to form an intimate polymer network.

Another embodiment of the present invention is the use of at least one plasticizer to modify and/or control the rate at which disposable materials degrade such that the disposal degradation rate is accelerated relative to the operative degradation rate. Plasticizers of the present invention are compounds that are incorporated into disposable materials of the present invention during, or after, polymerization. Plasticizers introduce pliability, flexibility and toughness into a polymer to an extent not typically found in a disposable material containing only a polymer or copolymer. Introduction of plasticizers into the polymer reduces the melt viscosity of the polymer and lowers the temperature, pressure, and shear rate required to melt-form the polymer. Plasticizers also prevent heat build-up and consequent discoloration and molecular weight decrease during processing steps, such as production and packaging. Further, plasticizers add impact resistance to the polymer. Plasticizers can increase or decrease polymer degradation rates and, thus, addition of plasticizers to a disposable material can be used to control the operative degradation rate of the material.

Plasticizers of the present invention can be either internal or external plasticizers. Internal plasticizers are part of the polymeric backbone itself or chemically bonded to the polymer backbone, whereas external plasticizers are discrete compounds that are not chemically bonded to the polymer. A method to produce polymers with plasticizers is described in co-pending U.S. patent application Ser. No. 07/579,005. Suitable plasticizers of the present invention include, but are not limited to, hydroxycarboxylic acids and cyclic esters thereof, oligomers of hydroxycarboxylic acids and cyclic esters thereof, dibasic acid esters, polyesters, aromatic ethers, aromatic esters, esters of relatively long chain acids, esters of relatively long chain alcohols, sulfonamides, tertiary amines, alkylene carbonates, keto-esters, ketones, compound with multiple ketone groups, ethers, other polar compounds, and mixtures thereof. Preferred plasticizers include α-hydroxy-carboxylic acids and cyclic esters thereof, oligomers of α-hydroxycarboxylic acids and cyclic esters thereof, lactones, dilactones, dibasic acid esters, low molecular weight polyesters, ketones, cyclic amides, diphenyl ether, diethyl phthalate, ethyl octoate, lauryl acetate, polypropylene glycol adipate, glyceryl diacetate, glyceryl triacetate, cyclododecanone, isophorone, other polar, nontoxic, nonfugitive compounds, and mixtures thereof. Glucose or sucrose ethers and esters are included, as are polyethylene glycol ethers and esters, glycerine diacetate N,N'-substituted amino acid esters and oligomers, and amides. More preferred hydrophilic plasticizers include lactic acid, L-lactide, D-lactide, D,L-lactide (wherein D,L-lactide includes the racemic isomers, the meso isomer, and/or mixtures thereof), glycolide, glycolic acid oligomers, lactic acid oligomers, glycolide oligomers, L-lactide oligomers, D-lactide oligomers, D,L-lactide oligomers, butyl lactate, ethyl lactate, diethyl adipate, polyethylene glycol succinate, epsilon-caprolactone, valerolactone, adipic acid esters, citric acid esters, glycol-alkyl esters, and mixtures thereof. More preferred hydrophobic plasticizers include stearyl esters, low-toxicity phthalates, phenyl ethers, phenyl esters, sebacic acid esters, and mixtures thereof. Oligomers are typically from about 2 to about 35 monomeric units. Typically, the disposable material contains from about 5 to about 50 weight percent plasticizer. A preferred amount of plasticizer in the disposable material is from about 10 to about 30 weight percent.

Another embodiment of the present invention is the modification of at least one structural characteristic of a disposable material in order to modify and/or control the rate at which the disposable material degrades such that the disposal degradation rate is accelerated relative to the operative degradation rate. The structure of the disposable material can be modified in a variety of ways including modifying the crystallinity, free volume, orientation, molecular weight (i.e., chain length), and/or surface area of the polymer. For example, a highly crystalline, oriented disposable material has a regular structure that is typically not very susceptible to degradation. As a disposable material loses crystallinity and orientation, the material becomes less ordered and has more "free volume" into which water can penetrate, leading to accelerated hydrolysis and degradation. For example, the rate at which a highly crystalline lactic acid polymer degrades is typically about two to three times longer than the rate at which an amorphous lactic acid polymer degrades.

Methods to obtain hydroxycarboxylic acid-containing disposable materials of varying degrees of crystallinity and orientation are described, for example, in U.S. patent application Ser. Nos. 07/579,005 and 07/579,465. Polymers can be oriented either uniaxially (i.e., the polymers line up in one direction) or biaxially (i.e., the polymers line up in two directions).

Crystallinity can be measured in a variety of ways including, but not limited, to X-ray diffraction and thermal analyses such as thermal gravimetric analysis and density scanning calorimetry. A preferred method is X-ray diffraction which gives quantitative measurements. Disposable materials of the present invention have crystallinities and orientations that are suitable for their applications; see, for example, co-pending, commonly assigned, patent application entitled "Degradable Polymer Composition," filed on Sep. 22, 1992, U.S. Ser. No. 07/950,854 (Attorney File No. 4042-26).

The free volume of disposable materials of the present invention can be measured using, for example, a free volume microprobe. Disposable materials of the present invention can have macroscopic free volumes, such as is found in foams; microscopic free volumes, which are small voids that can be seen with a microscope; and nanoscopic free volumes, which are very small voids that are created by the shape of an object, such as gas, as it exits the polymer. For example, a soluble or volatile substance, such as carbon dioxide, can be mixed into a polymer and later be removed by, for example, volatilization.

One method to modify the crystalline structure of a disposable material is to control the amount of residual monomer remaining in the polymer after polymerization. A polymer having a low amount of residual monomer has fewer acidic end groups if the monomer is an acid and less low molecular weight esters that readily form compounds with acid end groups if the monomer is an ester and hence, is less susceptible to hydrolytic degradation activated by acid groups than is a polymer having a high amount of residual monomer. The concentration of residual monomer affects not only the rate at which water penetrates the surface of the disposable material but also the rate of water penetration inside the amorphous structure of the polymer. In addition, high residual monomer concentrations can impede crystallization. The concentration of residual monomer in typical disposable materials of the present invention is from about 10 ppm to about 40 weight percent residual monomer in the disposable material. Preferably, the concentration of residual monomer is less than about 20 weight percent.

The degradation characteristics of a polymer can also be changed by modifying the size of the polymer. For example, a D,L-lactic acid polymer (PLA) having a molecular weight of over about 5,000 daltons is typically rigid and hard, whereas PLA having a molecular weight of less than about 5,000 daltons is typically semisolid and soft which allows increased water penetration compared to high molecular weight polymers. In addition, low molecular weight PLA polymers (i.e., polymers having shorter chain length) have more acid groups (i.e., free ends) per unit length than do high molecular weight polymers (i.e., polymers having a long chain length); such acid groups, as described above, can catalyze hydrolysis. The molecular weights of disposable materials of the present invention can depend on their applications; see, for example, co-pending, commonly assigned, patent application entitled "Degradable Polymer Composition," filed on Sep. 22, 1992, U.S. Ser. No. 07/950,854 (Attorney File No. 4042-26).

The structure of disposable materials of the present invention can also be modified by modifying the surface area of the disposable material. Materials with larger surface areas are typically more prone to degradation than are materials with smaller surface areas as there is an increased area through which compounds, such as water and acid, can penetrate. The surface area to volume ratio of disposable materials of the present invention depends on their use. For example, packaging materials usually have a thickness of about 0.5 to about 20 mil. Methods to increase the surface area include production of disposable materials with foamed structures (including foams with very small pores) through which water can penetrate.

Yet another embodiment of the present invention is the use of physical stress to modify and/or control the rate at which disposable materials degrade such that the disposal degradation rate is accelerated relative to the operative degradation rate. A disposable material is produced which begins to degrade when exposed to a physical stress, such as pressure (e.g., crumpling a package), torsion (e.g., twisting so as to disrupt disposable material), and stretching past the yield point. As long as yield stress is not applied to the disposable material, the disposable material's rate of degradation is very low. When stress is applied at the beginning of the disposal stage, such as twisting a package prior to throwing it away or breaking a barrier coating, the stress exposes the disposable material to degradation.

Since a rate-dependent step for hydrolysis of disposable materials of the present invention is diffusion of moisture into the polymer, one embodiment of the present invention is the use of at least one hydrophobic compound to modify and/or control the moisture penetration rate so that the disposal degradation rate is accelerated relative to the operative degradation rate. Hydrophobic compounds are compounds that have a low affinity for water. As such, they can protect hydroxycarboxylic acid-containing polymers from hydrolysis and, thus, reduce the degradation rate of disposable materials containing such polymers. Suitable hydrophobic compounds for use in the present invention include, but are not limited to: monomers and oligomers, including those comprising substituted hydroxycarboxylic acids and cyclic esters thereof; hydrophobic plasticizers, including hydroxycarboxylic acids or cyclic esters or oligomers thereof; other hydrophobic monomers or polymers that can be used as comonomers, copolymers, block copolymers or plasticizers; and mixtures thereof. Hydrophobic compounds can be incorporated directly into polymers, can be added in the form of internal or external plasticizers, and/or can be grafted (i.e., attached) to the polymer backbone. Methods to graft hydrophobic compounds to a polymer backbone include, but are not limited to, trifunctional monomers, grafting sites, and post-polymerization covalent attachment. Methods of polymerization, including copolymerization, both with and without plasticizers have been taught in co-pending U.S. application Ser. Nos. 07/579,000 by Sinclair, 07/579,005 by Sinclair, 07/579,460 by Sinclair et al., and 07/579,465 by Sinclair, all filed on Sep. 6, 1990, and, as referred to above, are incorporated by reference herein in their entirety.

Preferred hydrophobic compounds of the present invention include hydroxycarboxylic acids with long aliphatic chains, esters having long chain aliphatic or olefinic acids, esters having long chain alcohols, polyesters, glycerides, ketones, aromatic acids, aromatic ethers, aromatic esters, hydrophobic mineral fillers, and mixtures thereof. Hydrophobic compounds usually have a high ratio of carbon and hydrogen atoms to oxygen atoms. Preferred hydrophobic compounds of the present invention have an average of at least about three carbon atoms per oxygen atom (i.e., a carbon-to-oxygen ratio of about 3) because such compounds exhibit little water solubility. Examples of such compounds include: one or more long chain aliphatic acids or fatty acids, which can have a carbon chain having an odd or even number of carbon atoms. Suitable examples include α-hydroxyoctanoic acid, α-hydroxynonanoic acid, α-hydroxydecanoic acid, α-hydroxyundecanoic acid, α-hydroxydodecanoic acid, α-hydroxytridecanoic acid, α-hydroxymyristic acid, α-hydroxypentadecanoic acid, α-hydroxy-palmitic acid, α-hydroxyheptadecanoic acid, α-hydroxystearic acid, α-hydroxynonadecanoic acid, α-hydroxyarachidic acid, α-hydroxybehenic acid, α-hydroxylignoceric acid, α-hydroxycerotic acid, α-hydroxyoleic acid, α-hydroxy-linoleic acid, α-hydroxylinolenic acid, α-hydroxy-arachidonic acid, 2-ethylhexylcarboxylic acid, and other naturally-occurring hydroxycarboxylic acids; cyclic esters thereof; and a cyclic ester of α-hydroxyisobutyric acid. Other suitable hydrophobic compounds include one or more aromatic or dicarboxylic acids such as mandelic acid, benzylic acid, sebacic acid, azelaic acid, and their glycol esters. More preferred hydrophobic compounds are those with a carbon:oxygen ratio of at least about 6 which exhibit essentially no water solubility.

One embodiment of the present invention is the use of hydrophobic plasticizers to control the rate at which water penetrates into the resulting disposable material. The plasticizers can be added at a variety of concentrations. Preferably, disposable materials containing hydrophobic plasticizers contain from about 5 percent to about 50 percent plasticizer. The plasticizers, depending on their characteristics, may be added before or during formulation of the disposable material. Hydrophobic plasticizers can be used in the presence of lactide and/or lactic acid oligomers as long as the overall hydrophilic/lipophilic balance is high enough to impart sufficient hydrophobicity to keep the water concentration below a critical concentration, generally less than about 200 ppm by weight. Suitable plasticizers include, but are not limited to: esters of relatively long chain acids, such as ethyl laurate; esters of relatively long chain alcohols, such as lauryl acetate; low molecular weight polyesters, such as polypropylene glycol adipate; glyceryl triacetate; ketones, such as 2-undecanone, isophorone, and cyclododecanone; aromatic ethers or esters, such as alkylated polyglycol ethers or polyethylene adipate; and mixtures thereof.

In addition, copolymers of hydroxycarboxylic acid and hydrophobic polymers, such as polystyrene, polyethylene terephthalate (PET), diethyl phthalate (DEP), polyvinyl chloride (PVC), and polypropylene can be used to promote hydrophobicity. Copolymers can be produced by mixing at least two co-reactive monomers; at least two co-reactive polymer blocks; at least two polymers; two monomers or polymer blocks with a third monomer or polymer block that is reactive with each of the first two; or mixtures thereof. In order to enhance the compatibility of hydrophobic polymers and, for example, lactic acid or lactide polymers, during blending, compatibilizers may be used. Suitable compatibilizers include the use of a styrene-lactide copolymer with polystyrene, a PET-polylactide block copolymer with PET, a polyethylene-polylactide block copolymer with polyethylene, lactide with DEP, DEP-lactide with PVC, and a polypropylene-polylactide block copolymer with polypropylene. These can be grafted together or blocked by chain extension processes using reactive end groups.

If transparency of the resulting disposable material is not an issue, other hydrophobic compounds including minerals such as carbon blacks, mica, talc, silica, and titanium oxide can be used as fillers.

In a preferred embodiment, disposable materials of the present invention consist of an α-hydroxycarboxylic acid-containing polymer coated or laminated with a hydrophobic compound-containing material. Particularly preferred is a coating that is prone to abrasion. Such a coating protects the polymer from significant water penetration, and hence from significant degradation, during the operative stage of the disposable material. However, as the disposable material is used, it becomes scratched, and, upon disposal, the material is exposed to increased abrasion. Such abrasion allows water penetration of the coating which leads to accelerated degradation rate of the polymer, and hence, of the disposable material. An advantage of this embodiment is that the coating can be much more hydrophobic than can be a disposable material into which at least one hydrophobic compound has been blended. As increased amounts of hydrophobic compounds are blended into a disposable material, the material loses strength. Thus, the option of coating the material with a hydrophobic compound allows for the internal disposable material to be of desired strength and other characteristics. In one embodiment, a disposable material of the present invention is first coated with a compound that absorbs water and then is coated with a hydrophobic abrasion-prone coating.

Suitable hydrophobic coatings should be compatible with the hydroxycarboxylic acid-containing polymer. Examples of hydrophobic compounds with which to coat polymers include any of the compounds described above, and especially polyvinyl chloride, polyvinylidine chloride, polyethylene terephthalate, nitrocellulose, polystyrene, polyethylene, polypropylene, polyvinyl acetate, and mixtures thereof. Preferred hydrophobic compounds to use as a coating include polyvinyl chloride and polyethylene terephthalate.

The hydrophobicity of disposable materials of the present invention can be measured in a variety of ways, including Hydrophile-Lipophile Balance (HLB) and contact angle. The HLB is an expression of the relative amounts of the hydrophilic (water-loving or polar) and lipophilic (oil-loving or non-polar) groups in the disposable material without weighting their polarity strengths. A disposable material that is lipophilic (i.e., hydrophobic) in nature is assigned a low HLB (below 9.0, on a scale of 0 to 20 units). HLB measurements are useful in estimating whether a candidate additive will help to speed or retard water permeation. For example, the HLB value of polylactic acid is approximately 1 and that of polyglycolic acid is about 15. Lactide has an HLB of about 12 and glycolide has an HLB of about 15. A typical good plasticizer for polylactic acid is dimethyl adipate (HLB about 10); however this plasticizer does not function well with polyglycolic acid. A plasticizer that functions marginally with polylactic acid is lauronitrile, which has an HLB of about 3 and an extremely polar hydrophilic group. Preferably, the HLB values of a plasticizer should be within about 4 units, and more preferably within about 2 units, of the polymer to be plasticized. In certain circumstances, the range can be as broad as about 7 HLB units.

The contact angle is a measure of the ease with which the air that occupies the interface can be displaced by water. A standard method to measure contact angle is to place a droplet on the surface of the material to be tested and make a direct measurement with a microscope equipped with a goniometer (M. J. Rosen, Surfactants and Interfacial Phenomena, Wiley, 1978). Contact angle measurements are particularly useful in determining how soon a disposable material will start to degrade. A material with a high contact angle causes water and other hydrophilic substances to bead on the surface, thereby reducing penetration of the disposable material by such substances. Materials with contact angles of less than about 90 degrees are prone to degradation, whereas materials with contact angles of at least about 90 degrees, and up to about 180 degrees, usually repel moisture. In a preferred embodiment in which a disposable material is coated with a hydrophobic compound, the inner disposable material will have a relatively low contact angle (e.g., preferably less than about 90 degrees), whereas the coating will have a relatively high contact angle (e.g., preferably at least about 90 degrees).

Another embodiment of the present invention is the use of at least one end-capping agent to modify and/or control the rate at which disposable materials degrade such that the disposal degradation rate is accelerated relative to the operative degradation rate. While not being bound by theory, it is believed that polymers of hydroxycarboxylic acids degrade by two mechanisms: random scission within the polymer and back-biting of the terminal hydroxyl ends of the polymer. In addition, the carboxyl ends apparently promote degradation both by polarizing ester bonds and by providing acid groups that increase (i.e., accelerate) the rate of hydrolysis as it is believed that free carboxyl groups are surrounded by shells of water which promote degradation. As more carboxyl end groups are formed during hydrolysis, there are additional acid groups which trap and accumulate water. It is further believed that while reactive hydroxyl ends can be more responsible for enhancing degradation during melt processing, free carboxyl ends can be more responsible for degradation during the operative and disposal stages. As such, blocking carboxyl and/or hydroxyl groups of the disposable material is thought to retard degradation during the operative stage. As degradation proceeds during the disposal stage, however, new end groups will be exposed which will further enhance degradation.

In a preferred embodiment, carboxyl end groups of the disposable material are blocked by an end-capping agent which is typically added after polymer production. Suitable end-capping agents to block carboxyl groups include alcohols, chlorosilanes, alkyl chlorides, isocyanates, amines, methyl esters, and mixtures thereof. Preferred carboxyl end-capping agents include t-butyl alcohol, trimethyl chlorosilane, hexamethyldisilazane phenylisocyanate, and acetyl chloride.

Hydroxyl end groups can also be blocked by adding end-capping agents such as anhydrides, acid chlorides, and isocyanates. Preferred end-capping agents to block hydroxyl groups are anhydrides, such as acetic anhydride and stearic anhydride. Stearic anhydride is more preferred as addition of stearic groups increases the hydrophobicity of the disposable material.

The use of reversible end-capping agents that can be removed from the disposable material during the disposal stage allows for an accelerated disposal degradation rate of the disposable material upon removal of the agents. Such removal may be triggered by a change in the environment, such as an increase in moisture or temperature (e.g., steam autoclaving). Preferred reversible carboxyl end-capping agents include phenylisocyanate, acetyl-chloride, hexamethyldisilazane and trimethyl chlorosilane. Preferred reversible hydroxyl end-capping agents include phenyl isocyanate, acetic anhydride, and acetyl chloride.

Another embodiment of the present invention is cross-linking disposable materials of the present invention in order to modify and/or control the rate at which disposable materials degrade such that the disposal degradation rate is accelerated relative to the operative degradation rate. Cross-linking of polymers within the disposable material usually leads to slower degradation rates. While not being bound by theory, it is believed that cross-linking of polymers leads to tighter binding, thereby making it more difficult for water to penetrate the disposable material; in addition, cross-linking can reduce the rate at which polymer bonds are hydrolyzed.

Suitable cross-linking agents include, but are not limited to: tartaric acid; free-radical generators, such as peroxides and radiation; multifunctional chain extenders; trifunctional monomers; reactive pendant groups; and mixtures thereof.

Preferred cross-linking agents include tartaric acid, peroxides, hydroperoxides, trichloroisocyanurate, nadic anhydride, glycerine, pyromellitic dianhydride, triisocyanates, polyaniline, polyisocyanate, 1,3,5-triaminobenzene, bisphenol/diepoxide, polymerized allyl or vinyl-substituted dioxanedione, and mixtures thereof. Tartaric acid is a particularly preferred cross-linking agent because its structure leads to cross-link formation as it is being polymerized into tartaric acid polymers. As used herein, a tartaric acid polymer includes polymers containing tartaric acid, as well as salts, esters, amides, and cyclic esters thereof; the cyclic esters can contain two tartaric acids or one tartaric acid joined to another α-hydroxycarboxylic acid. Dihydroxy maleic anhydride is a preferred source of tartaric acid linkages in these cross-linked polymers. Tartaric acid can also be used to cross-link other hydroxycarboxylic acid-containing polymers.

The stage at which cross-linking is conducted depends on the cross-linking agent being used. For example, tartaric acid can be an integral part of the polymerization. Trifunctional monomers are usually incorporated during or after polymerization. Free-radical generators, such as peroxides and radiation, chain extenders, and pendant groups are typically used for crosslinking after polymer formation. In one embodiment, functional hydroxyl, isocyanate, or epoxy groups are added to polymers that are then cross-linked using, for example, melamine, epoxy resin, or polyols.

Yet another embodiment of the present invention is the addition of at least one source of microbial nutrients to a disposable material in order to modify and/or control the rate at which the disposable material degrades such that the disposal degradation rate is accelerated relative to the operative degradation rate. While the hydroxycarboxylic acid-containing polymers of the present invention can be degraded to monomers by hydrolysis, typically microorganisms, or chemically- or microbially-produced enzymes, are used to accomplish complete degradation of the polymers to, for example in the case of lactic acid, carbon dioxide and either water or methane. Disposable materials deposited in a landfill can attract microbial degradation by containing nutrients that promote the activity of microorganisms capable of degrading the materials. As used herein, the phrase "promote the activity of microorganisms" refers to the ability of the nutrients to enhance the rate at which the microorganisms grow and degrade disposable materials. Suitable nutrients include, but are not limited to, sources of carbohydrate, nitrogen, phosphate, sulfate, metals, and other salts. Typically, microorganisms can obtain carbon from the disposable materials, but in most cases, the disposable materials do not supply nitrogen, metals or salts. Thus, a preferred source of nutrients includes at least one of the following: a nitrogen source, a salt source, and a metal source. Also preferred are complex nutrients, such as vitamins and growth promotants, particularly for microorganisms that are not capable of producing such compounds from simple nutrients. Sources of nutrients can, for example, be incorporated into the polymer, grafted to the polymeric backbone of the disposable material, be microencapsulated, or be coated onto the surface of the disposable material. In one embodiment, nutrients can include compounds, such as hydroxycarboxylic acids with long aliphatic or fatty acid chains and isocyanates, which are added to the disposable material to control degradation in other ways.

In one embodiment, disposable materials of the present invention include polymers that contain amide functional groups, such as those formed from alpha amino acids. Such poly(esteramides) have excellent strength and can have their flexibility controlled by plasticization. In addition, the poly (esteramide) contains nitrogen-containing nutrients in a form that can be utilized by the microorganisms that conduct biodegradation reactions. Incorporation of amide groups accelerates disposal degradation rates because the degradation microenvironment (e.g., a fragment of a plastic container) can support a large microbial population. The microorganisms consume the polyester part of the molecules for energy and use the nitrogenous parts to make microbial protein, nucleotides, and other nitrogen-containing products needed by the microorganisms for growth and reproduction.

Plasticizers can also be sources of nitrogen-containing nutrients. For example, N-methyl pyrrolidinone can be used in the formulation to plasticize polymers of the present invention. Such a plasticizer can also provide a nitrogen source that can be used by the microorganisms more rapidly than nitrogen contained in a polymer backbone.

Another embodiment of the present invention is the inclusion in the disposable material of an indicator to detect whether degradation has occurred. Suitable indicators include those which detect pH and/or moisture changes and which indicate hydrolytic degradation by changes in color or cloudiness.

The following examples are provided for purposes of illustration and are not intended to limit the scope of the invention.

EXAMPLES

In the following examples, the base polymer that is used as the degradable polymer is a 90/10 weight ratio of L-lactide/D,L-lactide copolymer (referred to as the 90/10 copolymer), unless otherwise noted. Unless noted, polymers used in these examples were initially colorless, transparent thermoplastics when quenched from the melt as thin films of about 2- to about 10-mil thickness. Molecular weights were estimated by gas permeation chromatography (GPC), and referred to monodisperse polystyrene calibration standards. The weight-average molecular weights, $M_w$, are typically from about 150,000 to about 200,000 with $M_w/M_n$ values from about 1.8 to about 2.5, where $M_n$ refers to the number average molecular weight. In the examples, the polymers were subjected to various compositional and process changes. The effects of these changes on packaging and use degradation rates are noted and compared to disposal degradation rates.

Example 1

In this experiment, a 90/10 copolymer was plasticized with different compounds that are more or less hydrophobic. The 90/10 copolymer was melted and mixed on an open 2-roll mill at 330° F. for 10 minutes to remove, by volatilization, any residual lactide. An isothermal weight loss at 200° C. by thermal gravimetric analysis (TGA) revealed that the residual lactide was less than about 0.5 percent. In one case, 18 percent by weight of L-lactide was added to the melted copolymer and mixed at 330° F. on the mill roll until homogeneous. In another case, 18 percent oligomeric lactic acid (OLA), with an average degree of polymerization of about 2, was added in a similar manner until the mixture was homogeneous.

In each case, thin films, approximately 10-mil thick, were compression molded between plates at 300° F. to 330° F. The films, which were tough, foldable, colorless and transparent, were exposed to ambient indoor conditions until they became opaque and/or brittle to the touch, i.e., they shattered merely by gentle lifting and handling. The lactide-plasticized sample opacified and embrittled within 2 months while the OLA-plasticized sample required approximately 2 years to embrittle.

With reference to the plasticizers' hydrophobicity, lactide is slowly soluble in water while the OLA is insoluble in water. Similarly, if an even more hydrophobic plasticizer is used, e.g., diethyl phthalate, excellent plasticization was observed and the packaging and degradation rate prior to disposal was very slow since at least several years of shelf life were observed without noticeable change in physical properties.

Example 2

In this example, the effect of end-capping on degradation was observed. A 90/10 copolymer has two end-groups, one hydroxyl and one carboxyl. The hydroxyl end-group was capped using acetic anhydride according to the following method. Twenty grams (g) of the copolymer was dissolved in 200 milliliters (ml) of dry tetrahydrofuran, and 2.0 ml of pyridine and 4.0 ml of acetic anhydride added. The polymers were dissolved and the reaction proceeded with overnight refluxing. Controls were prepared, omitting the anhydride, using 200 ml of THF and 2.0 ml of pyridine. The polymers were isolated by precipitation in approximately one liter of stirred methanol to obtain a white, fibrous polymer that was washed three times, then vacuum dried overnight at 30° C. at 1 torr.

Films of about 5- to about 10-mil thickness (about 125 to about 250 microns) were prepared from the products and placed in an environmental chamber at about 90° F. (32° C.) and about 95 percent relative humidity for study of shelf-life stability.

Thermal stability of the copolymers was evaluated by thermal gravimetric analysis (TGA). By the TGA method, isothermal weight losses at 180° C. were recorded, and the percent weight loss per minute calculated from the slope of the depolymerization line.

NMR analysis showed that the acetic anhydride treated polymer was end-capped. Its weight loss at 180° C. was about 0.003 percent per minute while the control copolymer that was not end-capped revealed an approximate 0.008 percent per minute weight loss. Samples of films from these polymers were exposed in an environmental cabinet at about 90° F. and about 95 percent relative humidity. The non-end-capped sample became cloudy, sticky, and brittle, while the end-capped sample was virtually unchanged after 28 days.

In a separate experiment, a 90/10 copolymer was treated with diazomethane which end-capped the carboxyl group of the copolymer, as shown by NMR. Films of this material showed an isothermal weight loss of only about 0.002 weight percent per minute at 180° C. by TGA. When both end groups, (i.e., carboxyl and hydroxyl) were end-capped, the weight loss as determined by the same methods was about 0.003 weight percent per minute. Samples of films that were either carboxyl-end-capped or both carboxyl- and hydroxyl-end-capped were exposed to the same environmental chamber as described above and remained virtually unchanged after 28 days.

Example 3

The degradation rates of three separate copolymer blends, which consisted of 5 percent L-PLA, 10 percent lactide, and 1 percent fumaric acid, respectively, were compared during exposure to sea water. The results are shown in Table 1. Copolymers either with a lactide plasticizer or with an activator (fumaric acid) showed more severe degradation after 9–12 weeks than did the copolymer sample with L-PLA.

TABLE 1

Tensile Properties of Polylactide Film After Sea Water Exposure[a]

| Sample Composition | Exposure Time, weeks | Elastic Modulus, psi | 1% Secant Modulus, psi | Tensile Strength, psi |
|---|---|---|---|---|
| 95% 90/10 L-/ D,L 5% L- PLA | 0 | 304,722 | 292,020 | 7,649 |
|  | 3 | 314,566 | 300,578 | 7,096 |
|  | 6 | 317,050 | 317,050 | 7,314 |
|  | 9 | 227,644 | 230,284 | 6,214 |
|  | 12 | 355,302 | 343,061 | 3,881 |
| 90/10 L-/D,L 10% Plasticizer | 0 | 274,521 | 274,521 | 6,113 |
|  | 3 | 291,181 | 280,762 | 6,806 |
|  | 6 | 246,050 | 246,050 | 3,856 |
|  | 9 | 110,864 | 105,251 | 1,444 |
|  | 12 | 360,000 | 353,846 | 3,308 |
| 90/10 L-/D,L 1% Fumaric Acid | 0 | 299,597 | 297,546 | 7,053 |
|  | 3 | 291,759 | 291,439 | 6,471 |
|  | 6 | 318,313 | 318,313 | 6,896 |
|  | 9 | 225,828 | 223,310 | 6,142 |
|  | 12 | 69,979 | 139,957 | 807 |

[a]Exposure at Daytona Beach, Florida. Temperature range of sea water = 20–29° C.; Salinity range of sea water = 33.4–38.4; pH range = 7.2–7.9. Values are average of 6 specimens. Strain rate 1.0 in./in./min.

Example 4

Copolymers with different amounts of residual monomer resulting from different plasticizer compositions were composted. About 0.5 g of each copolymer was placed in 50 g of soil/compost, which had a total organic carbon of 3 percent, water-holding capacity of 55 percent, and a total aerobic count of $2 \times 10^7$ colony forming units (CFU) per gram. The samples were incubated 188 days at $23° \pm 2°$ C. The results, shown in Table 2, demonstrate that degradation, as determined by both molecular weight loss and physical property loss, was dependent on residual monomer amounts resulting from different plasticizer compositions.

TABLE 2

Results of Compost Bed Exposure

| Sample Description | Observations at 188 days |
|---|---|
| 90/10, L-/D,L; 8.7% residual monomer; $M_w = 128,000$; $M_n = 67,000$; $M_z =$ | Brittle, very fragile, only pieces remaining, |

TABLE 2-continued

Results of Compost Bed Exposure

| Sample Description | Observations at 188 days |
|---|---|
| 238,000; $M_w/M_n = 1.92$ | white, translucent |
| 90/10, L-/D,L; 19.7% residual monomer; $M_w = 134,000$; $M_n = 67,000$; $M_z = 252,000$; $M_w/M_n = 1.99$ | Brittle, very fragile, only pieces remaining, transparent but slight whiteness |
| 90/10, L-/D,L; 2–3% residual monomer; $M_w = 168,000$; $M_n = 80,000$; $M_z = 368,000$; $M_w/M_n = 2.09$ | Intact, flexible, transparent, no discoloration |

Example 5

This example shows the effects of cross-linking, stress, and coating on a poly(D,L-lactide) polymer. An approximately 10-mil film of poly(D,L-lactide) was overlaid with a thin film of cross-linked poly(D,L-lactide). The latter was laid down in a plasma polymerization chamber and was a fraction of a mil thick. The laminate was immersed in boiling water which digested to soluble products all but a thin layer of cross-linked polymer, which remained intact.

A similar laminate that was stressed to crack the overlayer showed more rapid water penetration when immersed in water or exposed to humid air.

Example 6

The degradation rate of poly(D,L-lactide), poly(L-lactide), and a 50/50 copolymer of L-lactide/glycolide was compared to demonstrate the effect of polymer and copolymer composition. Thin films of these polymers which were exposed to humid ambient air degraded as follows:

1. 50/50 copolymer—about one month to opacity and embrittlement
2. Poly(D,L-lactide)—about 3 months to opacity and embrittlement
3. Poly(L-lactide)—no change after 6 months.

All of the polymers initially contained about 4% residual monomers. The poly(L-lactide) was extremely crystalline and resisted invasion by water, and subsequent hydrolysis, for more than 2 years.

Example 7

Crystalline and noncrystalline PLA's were composted as shown in Table 3. The crystalline sample showed no molecular weight reduction in 3 months while the amorphous sample showed an approximate 4-fold reduction in molecular weight.

In a separate experiment, a 90/10 copolymer was compression molded at 330° F. into a slab with dimensions of 25×62×7 mm and allowed to cool slowly by simply turning off the heat to the press. The sample took several hours to cool to room temperature. It was then removed from the press and found to be substantially opaque, an example of spherulitic crystallization. The slab showed no visual changes of degradation after 2 years of exposure to ambient, indoor air. By way of contrast, a 90/10 copolymer molded into amorphous, transparent films that were about 10-mil thick showed obvious degradation under the same conditions in about 2 to 14 months, depending on the residual monomer content.

TABLE 3

Degradability of Copolymers in Compost Bed[a]
Before/After Compost

| Sample Composition | 90/10, L-/D,L-copolymer[b,d] | 90/10, thick sample[c,e] |
|---|---|---|
| $M_n$, in 1000s | 25.5/23.0 | 82.5/24.1 |
| $M_w$ in 1000s | 47.3/47.3 | 119/65.8 |
| $M_z$ in 1000s | 70.5/73.0 | 383/115 |
| $M_w/M_n$ | 1.8/2.1 | 2.4/2.7 |
| Res. Mon., % | 8.3/6.2 | 7.5/3.7 |

[a]3 months in compost bed
[b]10–13-mil film
[c]10–13-mil sheet
[d]Initially crystalline, and crystalline after compost exposure
[e]Initially amorphous, and crystalline after compost exposure

Example 8

A 90/10 copolymer, having a $M_w$=166,000 and residual lactide content of 1.89 percent, was pressed into thin films. Specimens were uniaxially drawn 3 to 4 times at 80° C. and heat set at 80° to 110° C. The samples were placed in an environmental cabinet at 100° F. and 90 percent relative humidity. The oriented, heat-set films took 53 days to embrittle, at which time their $M_w$ was approximately 56,000. The unoriented control sample was very cloudy and sticky in two weeks and its $M_w$ was about 20,000 after 53 days.

Example 9

The following example demonstrates the usefulness of adding a microencapsulated compound to disposable materials of the present invention. Crystals of fumaric acid are reduced in size to less than 10 microns in an attritor. The powder (1.2 grams, 0.01 moles) is encapsulated in 90/10 L-lactide/D,L-lactide by melting the polymer (which has an $M_w$ of about 200,000) and stirring the fumaric acid (sublimation point=200° C.), which is at 25° C., into the melt that is held at 170° C. The mixture is run through a pelletizer to generate pellets that contain particles of fumaric acid.

A Baker Perkins Extruder is employed to make samples of 10-mil film from a blend (50-to-1) of the above pellets with 90/10 L-lactide, D,L-lactide pellets. Control samples consisting of film with the same specifications but without the activator are made on the same day.

The physical properties and degradation rates of the activated samples and the control samples are measured and compared. The physical properties include tensile strength and elongation tests. Degradation is measured by GPC measurements on film samples that are exposed to 95° F. and 95 percent relative humidity. Six replicates of each film are used to attain statistical validity.

The activated samples initiate degradation before the control samples and degrade faster throughout the test. The GPC molecular weights show that the reaction is autocatalytic. Both opacity and physical property measurements confirm the GPC results.

Example 10

The following example further demonstrates the usefulness of microencapsulated activator compounds.

Fumaric acid (1.2 grams, 0.01 mole) is encapsulated in cellulose acetate butyrate. The particle size distribution is 10 microns to 25 microns. The capsules are dispersed in molten poly(90/10 L-lactide/D,L-lactide) that is held at 170° C. The mixture is fed into a foam extruder, along with carbon dioxide.

The treated foam has a density of approximately 5 lb/cu ft. Six replicates of control foams and acid-capsule-treated foams are exposed in an environmental degradation chamber at 95° F. and 95 percent relative humidity. The treated foams show rapid loss of molecular weight and begin to degrade before control foams which lack activator.

Example 11

The following example demonstrates the usefulness of adding blotting compounds to disposable materials of the present invention.

Sodium bicarbonate (2 grams, 0.01 mole) is micronized to fine particles. The particles are stirred into 500 grams of molten poly(90/10 L-lactide/D,L-lactide) that is held at 170° C. The dispersion is extruded immediately into a film that is quenched.

The film containing the sodium bicarbonate dispersion is evaluated by mechanical strength tests against a control that consists of the same composition except that the sodium bicarbonate is omitted. The initial molecular weights of the control and the sodium bicarbonate-treated film are also compared. Both polymer samples have MW's of about 150,000. Microscopy shows that the sodium bicarbonate particles are in the 1 to 10 micron range.

Six replicates of the control films and the sodium bicarbonate-treated films are exposed in an environmental degradation chamber at 95° F. and 95 percent relative humidity. The small bubbles that are generated by the formation and escape of carbon dioxide become water accumulation sites, as shown by optical microscopy.

The molecular weight of the treated samples (as measured by GPC) declines less during the early stages of exposure, but increases late in the exposure test (i.e., after the blotting compound is saturated,) to become accelerated compared to the control samples.

Example 12

The following example demonstrates the effect of adding nutrients to a disposable material of the present to make a 10-mil film that exhibits good tensile strength and elongation.

The degradation of the 10-mil poly(esteramide) film is tested with a culture of bacteria against a control of 90/10 L-lactide/D,L-lactide at the same thickness. The experimental design includes six replicates of each treatment. Minimal nitrogen is added to both microenvironments. Cell counts are made on 1 square centimeter samples of each film. Evolution of carbon dioxide is measured in a Warburg Apparatus.

The bacterial growth on the poly(esteramide) samples far exceeds that of the control samples. The amount of carbon dioxide is nearly equal, apparently reflecting conversion of part of the substrate to additional biomass.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. A method for reducing waste accumulation comprising using an environmentally degradable disposable material, wherein said material comprises a hydroxycarboxylic acid-containing polymer and wherein said material degrades hydrolytically during storage, use and disposal stages in a controlled manner such that the disposal degradation rate of said material is accelerated relative to the average of the storage and use degradation rates of said material, and wherein said average of said storage and said use degradation rates is less than about 50 percent of said disposal degradation rate.

2. The method of claim 1, wherein said waste is selected from the group consisting of landfill waste, water waste, and landscape surface waste.

3. The method of claim 1, wherein said degradation rates comprise changes in the molecular weight of said disposable material over time.

4. The method of claim 3, wherein said average of said storage and said use gradation rates is less than about 33 percent of said disposal degradation rate.

5. The method of claim 3, wherein said average of said storage and said use degradation rates is less than about 10 percent of said disposal degradation rate.

6. The method of claim 3, wherein said average of said storage and said use degradation rates is less than about 5 percent of said disposal degradation rate.

7. The method of claim 1, wherein said disposable material is at least about 98 percent hydrolytically degraded within about ten years after discard.

8. The method of claim 1, wherein said disposable material is at least about 98 percent hydrolytically degraded within about five years after discard.

9. The method of claim 1, wherein said disposable material is at least about 98 percent hydrolytically degraded within about three years after discard.

10. The method of claim 1, wherein said disposable material is hydrolytically degraded to monomers and oligomers essentially about or less than about 600 daltons molecular weight.

11. The method of claim 1, wherein said disposable material is further degraded by biological degradation.

12. The method of claim 1, wherein said disposable material is further degraded by microbial degradation.

13. The method of claim 1, wherein said disposable material is further biologically degraded to essentially carbon dioxide and water.

14. The method of claim 1, wherein said disposable material is further biologically degraded to essentially carbon dioxide and methane.

15. The method of claim 1, wherein said disposable material is selected from the group consisting of films, foams, coatings, molded articles, extruded articles, nonwoven fibers, pellets, powders, laminates, and adhesives.

16. The method of claim 1, wherein said disposable material is selected from the group consisting of films, foams, coatings, and molded articles.

17. The method of claim 1, wherein said disposable material comprises a packaging material.

18. The method of claim 1, wherein said controlled manner of hydrolytic degradation is achieved by adding at least one activator compound to said disposable material, wherein sa activator compound accelerates degradation of said disposable material.

19. The method of claim 18, wherein said activator compound is selected from the group consisting of an acidic compound, a basic compound that generates hydroxyl ions when exposed to water, a moisture-containing compound, and water.

20. The method of claim 18, wherein said activator compound is selected from the group consisting of fumaric acid, succinic acid, tartaric acid, malic acid, adipic acid, citric acid, glutamic acid, methane sulfonic acid, phosphoric acid, polyphosphoric acid, lactic acid oligomers, water, and mixtures thereof.

21. The method of claim 18, wherein said activator compound is selected from the group consisting of sodium bicarbonate, sodium carbonate, potassium bicarbonate, potassium carbonate, calcium hydroxide, ammonium borate, and mixtures thereof.

22. The method of claim 18, said activator compound is selected from the group consisting of water, starch-based hydrophilic polymers, cellulose-based hydrophilic polymers, hydrates of inorganic acids or salts thereof, hydrates of organic acids or salts thereof, and mixtures thereof.

23. The method of claim 18, said activator compound is blended with said material.

24. The method of claim 18, wherein said material is coated or laminated with said activator compound.

25. The method of claim 18, wherein said activator compound is microencapsulated.

26. The method of claim 18, wherein said activator compound is microencapsulated in a capsule comprising a capsule formulation selected from the group consisting of polylactides, polylactic acids, amyloses, ethyl cellulose, polyethylene terephthalate, aliphatic polyesters, and cellulose acetate butyrate.

27. The method of claim 25, wherein said activator compound is released from microencapsulation upon exposure to pressure, abrasion, heat, moisture or acid.

28. The method of claim 1, wherein said controlled manner of hydrolytic degradation is achieved by adding at least one blotting compound to said disposable material, wherein said blotting compound absorbs moisture or degradation products that promote degradation.

29. The method of claim 27, said blotting compound is selected from the group consisting of water grabbers, at least one alkaline compound that neutralizes acid, dry mineral fillers, and mixtures thereof.

30. The method of claim 27, wherein said blotting compound is microencapsulated in a capsule, wherein said capsule is susceptible to degradation by water or acid.

31. The method of claim 1, wherein said controlled manner of hydrolytic degradation is achieved by coating said disposable material with at least one coating compound to form a coat around said disposable material.

32. The method of claim 31, wherein said coat is prone to abrasion.

33. The method of claim 31, wherein said coating compound is hydrophobic.

34. The method of claim 31, wherein said coat has a contact angle of at least about 90 degrees.

35. The method of claim 31, wherein said step of coating comprises laminating.

36. The method of claim 1, wherein said controlled manner of hydrolytic degradation is achieved by producing a disposable material comprising at least one copolymer selected from the group consisting of copolymers comprising a mixture of at least two polymers, copolymers comprising a mixture of monomers, copolymers comprising a mixture of polymer blocks, an copolymers comprising a mixture of monomers and polymer blocks.

37. The method of claim 36, wherein said monomer is selected from the group consisting of hydroxycarboxylic acids and cyclic esters thereof, cyclic carbonates, dicarboxylic acids, anhydrides, diisocyanates, glycols, oligomeric polyalkylene adipates, and mixtures thereof.

38. The method of claim 36, wherein said monomer is selected from the group consisting of cyclic esters of hydroxycarboxylic acids, dilactones, cyclic carbonates, and mixtures thereof.

39. The method of claim 36, wherein said monomer is selected from the group consisting of L-lactide, D-lactide, D,L-lactide, glycolide, 2-methyl glycolide, tetramethyl glycolide, dioxanone, caprolactone, ethylene carbonate, propylene carbonate, and mixtures thereof.

40. The method of claim 36, wherein said polymer block is selected from the group consisting of hydroxycarboxylic acid polymers, polymers of cyclic esters of hydroxycarboxylic acids, alkyl ester polymers, alkylene carbonate polymers, cyclic carbonate polymers, polyethylene glycols, polyethylene terephthalates, phthalate esters, polyethylenes, polystyrenes, polyvinyl chlorides, polypropylenes, and mixtures thereof.

41. The method of claim 36, wherein said polymer block is selected from the group consisting of α-hydroxycarboxylic acid polymers, polymers of cyclic esters of α-hydroxycarboxylic acids, lactone polymers, dilactone polymers, and cyclic carbonate polymers, and mixtures thereof.

42. The method of claim 36, wherein said polymer block is selected from the group consisting of lactic acid polymers, glycolic acid polymers, L-lactide polymers, D-lactide polymers, D,L-lactide polymers, glycolide polymers, polyethylene terephthalates, adipic acid ethylene-glycol polymers, epsilon-caprolactone polymers, delta-valerolactone polymers, and mixtures thereof.

43. The method of claim 36, wherein said copolymer comprising an interpenetrating network of at least two polymers.

44. The method of claim 1, wherein said controlled manner of hydrolytic degradation is achieved by adding at least one plasticizer to said disposable material.

45. The method of claim 44, wherein said plasticizer is selected from the group consisting of internal plasticizers and external plasticizers.

46. The method of claim 44, wherein said plasticizer is selected from the group consisting of hydroxycarboxylic acids and cyclic esters thereof, oligomers of hydroxycarboxylic acids and cyclic esters thereof, dibasic acid esters, polyesters, aromatic ethers, aromatic esters, esters of relatively long chain acids, esters of relatively long chain alcohols, sulfonamides, tertiary amines, alkylene carbonates, keto-esters, ketones, compounds having multiple ketone groups, ethers, and mixtures thereof.

47. The method of claim 44, wherein said plasticizer is selected from the group consisting of α-hydroxy-carboxylic acids and cyclic esters thereof, oligomers of α-hydroxycarboxylic acids and cyclic esters thereof, lactones, dilactones, dibasic acid esters, low molecular weight polyesters, diphenyl ether, diethyl phthalate, ethyl octoate, lauryl acetate, polypropylene glycol adipate, glyceryl diacetate, glyceryl triacetate, cyclododecanone, isophorone, glucose ethers, sucrose ethers, polyethylene glycol ethers, polyethylene glycol esters, and mixtures thereof.

48. The method of claim 44, wherein said plasticizer is selected from the group consisting of lactic acid, L-lactide, D-lactide, D,L-lactide, glycolide, glycolic acid oligomers, lactic acid oligomers, glycolide oligomers, L-lactide oligomers, D-lactide oligomers, D,L-lactide oligomers, butyl lactate, ethyl lactate, diethyl adipate, polyethylene glycol succinate, epsilon-caprolactone, valerolactone, adipic acid esters, citric acid esters, glycol-alkyl esters, stearyl esters, phthalates, phenyl ethers, phenyl esters, and mixtures thereof.

49. The method of claim 1, wherein said controlled manner of hydrolytic degradation is achieved by a process selected from the group consisting of decreasing the crystallinity of said material, increasing the free volume of said material, decreasing the orientation of said material, decreasing the molecular weight of said material, increasing the surface area of said material, and mixtures thereof.

50. The method of claim 49, wherein said process of modifying the crystallinity of said material comprises aligning said material in a uniaxial or biaxial orientation.

51. The method of claim 1, wherein said material has a residual monomer concentration of from about 10 ppm to about 40 weight percent.

52. The method of claim 1, wherein said controlled manner of hydrolytic degradation is achieved by applying a stress to said material upon disposal of said material, wherein said stress initiates accelerated degradation of said material.

53. The method of claim 1, wherein said controlled manner of hydrolytic degradation is achieved by adding at least one hydrophobic compound to said disposable material.

54. The method of claim 53, wherein said hydrophobic compound has a carbon-to-oxygen ratio of at least about three carbon molecules per oxygen molecule.

55. The method of claim 53, wherein said hydrophobic compound has a carbon-to-oxygen ratio of at least about six carbon molecules per oxygen molecule.

56. The method of claim 53, wherein said hydrophobic compound is grafted to the polymeric backbone of said material.

57. The method of claim 53, wherein said hydrophobic compound is coated onto said material to form a hydrophobic coating.

58. The method of claim 57, wherein said hydrophobic coating has a contact angle of at least about 90 degrees.

59. The method of claim 53, said hydrophobic compound comprises a plasticizer.

60. The method of claim 53, wherein said hydrophobic compound is selected from the group consisting of monomers, polymer blocks, polymers, copolymers, and mixtures thereof.

61. The method of claim 53, wherein said disposable material further comprises a compatibilizer.

62. The method of claim 53, wherein said disposable material is coated or laminated with said hydrophobic compound.

63. The method of claim 53, wherein said hydrophobic compound is selected from the group consisting of hydroxycarboxylic acids having long aliphatic chains, esters having long chain aliphatic acids, esters having long chain oleic acids, esters having long chain alcohols, polyesters, glycerides, ketones, aromatic acids, aromatic ethers, aromatic esters, mineral fillers, and mixtures thereof.

64. The method of claim 1, wherein said controlled manner of hydrolytic degradation is achieved by adding at least one end-capping agent to said material.

65. The method of claim 64, wherein said end-capping agent is selected from the group consisting of alcohols, chlorosilanes, alkyl chlorides, acid chlorides, isocyanates, amines, methyl esters, and mixtures thereof.

66. The method of claim 64, said end-capping agent is reversible.

67. The method of claim 1, wherein said controlled manner of degradation is achieved by cross-linking said disposable material.

68. The method of claim 67, wherein said step of cross-linking is accomplished using a cross-linking agent selected from the group consisting of tartaric acid, free-radical generators, multifunctional chain extenders, trifunctional monomers, reactive pendant groups, and mixtures thereof.

69. The method of claim 67, said disposable material comprises a tartaric acid polymer.

70. The method of claim 12, wherein said microbial degradation is augmented by adding at least one source of nutrients to said disposable material, wherein said nutrients promote the activity of a microorganism that degrades said disposable material.

71. The method of claim 70, wherein said nutrients are grafted to the polymeric backbone of said material.

72. The method of claim 70, wherein said nutrients are microencapsulated.

73. The method of claim 1, wherein said hydroxy-carboxylic acid is an α-hydroxycarboxylic acid.

74. The method of claim 1, wherein said hydroxy-carboxylic acid is selected from the group consisting of lactic acid, glycolic acid, tartaric acid, malic acid, mandelic acid, benzylic acid, hydroxyvaleric acid, 1-hydroxy-1-cyclohexane carboxylic acid, 2-hydroxy-2-(2-tetrahydrofuranyl) ethanoic acid, 2-hydroxy-2-(2-furanyl) ethanoic acid, 2-hydroxy-2-phenylpropionic acid, 2-hydroxy-2-methylpropionic acid, 2-hydroxy-2-methylbutanoic acid, 2-hydroxy-2-ethylhexylcarboxylic acid, α-hydroxy-butyric acid, α-hydroxyisobutyric acid, α-hydroxypentanoic acid, α-hydroxyhexanoic acid, α-hydroxyheptanoic acid, α-hydroxyoctanoic acid, α-hydroxynonanoic acid, α-hydroxy-decanoic acid, α-hydroxydodecanoic acid, α-hydroxymyr-istic acid, α-hydroxypalmitic acid, α-hydroxystearic acid, α-hydroxyarachidic acid, α-hydroxybehenic acid, α-hydroxylignoceric acid, α-hydroxycerotic acid, α-hydroxyoleic acid, α-hydroxylinoleic acid, α-hydroxylinolenic acid, α-hydroxyarachidonic acid, α-hydroxypelargonic, α-hydroxyundecanoic acid, α-hydroxytridecanoic acid, α-hydroxypentadecanoic acid, α-hydroxyheptadecanoic acid, α-hydroxynonadecanoic acid, and mixtures thereof.

75. The method of claim 1, wherein said hydroxy-carboxylic acid is selected from the group consisting of lactic acid, glycolic acid, tartaric acid, malic acid, mandelic acid, benzylic acid, hydroxyvaleric acid, α-hydroxybutyric acid, α-hydroxyoctanoic acid, α-hydroxystearic acid, and mixtures thereof.

76. The method of claim 1, wherein said hydroxy-carboxylic acid is selected from the group consisting of lactic acid, glycolic acid, and mixtures thereof.

77. The method of claim 1, wherein said disposable material is selected from the group consisting of lactones, aliphatic esters of glycols, aliphatic esters of dicarboxylic acids; and mixtures thereof.

78. The method of claim 1, wherein said disposable material comprises a polymer selected from the group consisting of polylactic acids, polylactides, polyglycolic acids, polyglycolides, substituted polyglycolic acids, substituted polyglycolides, caprolactone polymers, valerolactone polymers, and copolymers thereof.

79. A method for producing an environmentally degradable disposable material comprising:

(I) providing a material comprising a hydroxycarboxylic acid-containing polymer that hydrolytically degrades during operative and disposal stages in a controlled manner such that the disposal degradation rate of said material is accelerated relative to the operative degradation rate of said material, and wherein the operative degradation rates is less than about 50 percent of the disposal degradation rate; and (II) selecting at least one step from the group consisting of:
(a) adding at least one activator compound to said material;
(b) adding at least one blotting compound to said material;
(c) coating said material with at least one coating compound;
(d) producing a material comprising a copolymer;
(e) adding at least one platicizer to said material;
(f) decreasing the crystallinity of said material;
(g) increasing the free volume of said material;
(h) decreasing the orientation of said material;
(i) decreasing the molecular weight of said material;
(j) increasing the surface area of said material
(k) applying a stress to said material;
(l) adding at least one hydrophobic compound to said material;
(m) adding at least one end-capping agent to said material; and
(n) cross-linking said material.

80. The method of claim 79, wherein said material is further degraded by biological degradation.

81. The method of claim 79, wherein said material is further degraded by microbial degradation.

82. The method of claim 81, wherein said microbial degradation is augmented by adding a least one source of nutrients to said material.

83. The method of claim 79, wherein said hydroxy-carboxylic acid is an α-hydroxycarboxylic acid.

84. The method of claim 79, said hydroxy-carboxylic acid is selected from the group consisting of lactic acid, glycolic acid, tartaric acid, malic acid, mandelic acid, benzylic acid, hydroxyvaleric acid, 1-hydroxy-1-cyclohexane carboxylic acid, 2-hydroxy-2-(2-tetrahydrofuranyl) ethanoic acid, 2-hydroxy-2-(2-furanyl) ethanoic acid, 2-hydroxy-2-phenylpropionic acid, 2-hydroxy-2-methylpropionic acid, 2-hydroxy-2-methyl-butanoic acid, 2-hydroxy-2-ethylhexylcarboxylic acid, α-hydroxybutyric acid, α-hydroxyisobutyric acid, α-hydroxy-pentanoic acid, α-hydroxyhexanoic acid, α-hydroxyheptanoic acid, α-hydroxy-octanoic acid, α-hydroxynonanoic acid, α-hydroxydecanoic acid, α-hydroxydodecanoic acid, α-hydroxymyristic acid, α-hydroxypalmitic acid, α-hydroxystearic acid, α-hydroxyarachidic acid, α-hydroxy-behenic acid, α-hydroxylignoceric acid, α-hydroxy-cerotic acid, α-hydroxyoleic acid, α-hydroxylinoleic acid, α-hydroxylinolenic acid, α-hydroxyarachidonic acid, α-hydroxypelargonic, α-hydroxyundecanoic acid, α-hydroxytridecanoic acid, α-hydroxypentadecanoic acid, α-hydroxyheptadecanoic acid, α-hydroxy-nonadecanoic acid, and mixtures thereof.

85. The method of claim 79, wherein said hydroxy-carboxylic acid is selected from the group consisting of lactic acid, glycolic acid, tartaric acid, malic acid, mandelic acid, benzylic acid, hydroxyvaleric acid, α-hydroxybutyric acid, α-hydroxyoctanoic acid, α-hydroxystearic acid and mixtures thereof.

86. The method of claim 79, wherein said hydroxy-carboxylic acid is selected from the group consisting of lactic acid, glycolic acid, and mixtures thereof.

87. The method of claim 79, wherein said disposable material is selected from the group consisting of lactones, aliphatic esters of glycols, aliphatic esters of dicarboxylic acids; and mixtures thereof.

88. The method of claim 79, wherein said disposable material comprises a polymer selected from the group consisting of polylactic acids, polylactides, polyglycolic acids, polyglycolides, substituted polyglycolic acids, substituted polyglycolides, caprolactone polymers, valerolactone polymers, and copolymers thereof.

89. The method of claim 79, wherein said disposable material is selected from the group consisting of films, foams, coatings, molded articles, extruded articles, nonwoven fibers, pellets, powders, laminates, and adhesives.

90. The method of claim 79, wherein said disposable material is selected from the group consisting of films, foams, coatings, and molded articles.

91. The method of claim 79, wherein said disposable material comprises a packaging material.

92. The method of claim 79, wherein said degradation rates comprise changes in the molecular weight of said disposable material over time.

93. The method of claim 92, wherein said operative degradation rate is less than about 33 percent of said disposal degradation rate.

94. The method of claim 92, wherein said operative degradation rate is less than about 10 percent of said disposal degradation rate.

95. The method of claim 92, wherein said operative degradation rate is less than about 5 percent of said disposal degradation rate.

96. The method of claim 79, wherein said disposable material is at least about 98 percent hydrolytically degraded within about ten years after discard.

97. The method of claim 79, wherein said disposable material is at least about 98 percent hydrolytically degraded within about five years after discard.

98. The method of claim 79, wherein said disposable material is at least about 98 percent hydrolytically degraded within about three years after discard.

99. The method of claim 79, wherein said disposable material is further biologically degraded to essentially carbon dioxide and water.

100. The method of claim 79, wherein said disposable material is further biologically degraded to essentially carbon dioxide and methane.

101. An environmentally degradable disposable material comprising a hydroxycarboxylic acid-containing polymer, wherein said material degrades hydrolytically during operative and disposal stages in a controlled manner such that the disposal degradation rate of said material is accelerated relative to the operative degradation rate of said material, and wherein said operative degradation rate is less than about 50 percent of said disposal degradation rate.

102. The disposable material of claim 101, wherein said hydroxycarboxylic acid is an α-hydroxy-carboxylic acid.

103. The disposal material of claim 101, wherein said hydroxycarboxylic acid is selected from the group consisting of lactic acid, glycolic acid, tartaric acid, malic acid, mandelic acid, benzylic acid, hydroxyvaleric acid, 1-hydroxy-1-cyclohexane carboxylic acid, 2-hydroxy-2-(2-tetrahydrofuranyl) ethanoic acid, 2-hydroxy-2-(2-furanyl) ethanoic acid, 2-hydroxy-2-phenylpropionic acid, 2-hydroxy-2-methyl-propionic acid, 2-hydroxy-2-methylbutanoic acid, 2-hydroxy-2-ethylhexylcarboxylic acid, α-hydroxy-butyric acid, α-hydroxyisobutyric acid, α-hydroxy-pentanoic acid, α-hydroxyhexanoic acid, α-hydroxy-heptanoic acid, α-hydroxyoctanoic acid, α-hydroxy-nonanoic acid, α-hydroxydecanoic acid, α-hydroxy-dodecanoic acid, α-hydroxymyristic acid, α-hydroxy-palmitic acid, α-hydroxystearic acid, α-hydroxyarach-idic acid, α-hydroxybehenic acid, α-hydroxylig-noceric acid, α-hydroxycerotic acid, α-hydroxyoleic acid, α-hydroxylinoleic acid, α-hydroxylinolenic acid, α-hydroxyarachidonic acid, α-hydroxypelargonic, α-hydroxyundecanoic acid, α-hydroxytridecanoic acid, α-hydroxypentadecanoic acid, α-hydroxyheptadecanoic acid, α-hydroxynonadecanoic acid, and mixtures thereof.

104. The disposable material of claim 101, wherein said hydroxycarboxylic acid is selected from the group consisting of lactic acid, glycolic acid, tartaric acid, malic acid, mandelic acid, benzylic acid, hydroxyvaleric acid, α-hydroxybutyric acid, α-hydroxyoctanoic acid, α-hydroxystearic acid, and mixtures thereof.

105. The disposable material of claim 101, wherein said hydroxy-carboxylic acid is selected from the group consisting of lactic acid, glycolic acid, and mixtures thereof.

106. The disposable material of claim 101, wherein said disposable material is selected from the group consisting of lactones, aliphatic esters of glycols, aliphatic esters of dicarboxylic acids; and mixtures thereof.

107. The disposable material of claim 101, wherein said disposable material comprises a polymer selected from the group consisting of polylactic acids, polylactides, polyglycolic acids, polygly-colides, substituted polyglycolic acids, substituted polyglycolides, caprolactone polymers, valerolactone polymers, and copolymers thereof.

108. The disposable material of claim 101, wherein said disposable material is selected from the group consisting of films, foams, coatings, molded articles, extruded articles, nonwoven fibers, pellets, powders, laminates, and adhesives.

109. The disposable material of claim 101, wherein said disposable material is selected from the group consisting of films, foams, coatings, and molded articles.

110. The disposable material of claim 101, wherein said disposable material comprises a packaging material.

111. The disposal material of claim 101, wherein said degradation rates comprise changes in the molecular weight of said disposable material over time.

112. The disposable material of claim 111, wherein said operative degradation rate is less than about 33 percent of said disposal degradation rate.

113. The disposable material of claim 111, wherein said operative degradation rate is less than about 10 percent of said disposal degradation rate.

114. The disposable material of claim 111, wherein said operative degradation rate is less than about 5 percent of said disposal degradation rate.

115. The disposable material of 101, wherein said material is capable of being about 100 percent hydrolytically degraded after discard.

116. The disposable material of claim 101, wherein said material is at least about 98 percent hydrolytically degraded within about ten years after discard.

117. The disposable material of claim 101, wherein said material is at least about 98 percent hydrolytically degraded within about five years after discard.

118. The disposable material of claim 101, wherein said material is at least about 98 percent hydrolytically degraded within about three years after discard.

119. The disposable material of claim 101, wherein said disposable material is further capable of being degraded by biological degradation.

120. The disposable material of claim 101, wherein said disposable material is further capable of being degraded by microbial degradation.

121. The disposable material of claim 101, wherein said disposable material is further capable of being biologically degraded to essentially carbon dioxide and water.

122. An environmentally degradable disposable material comprising a hydroxycarboxylic acid-containing polymer, wherein said material degrades hydrolytically during operative and disposal stages in a controlled manner such that the disposal degradation rate of said material is accelerated relative to the operative degradation rate of said material, wherein said operative degradation rate is less than about 50 percent of said disposal degradation rate and wherein said material is produced by a method comprising at least one step selected from the group consisting of:

(a) adding at least one activator compound to said material;

(b) adding at least one blotting compound to said material;

(c) coating said material with at least one coating compound;

(d) producing a material comprising a copolymer;

(e) adding at least one platicizer to said material;

(f) decreasing the crystallinity of said material;

(g) increasing the free volume of said material;

(h) decreasing the orientation of said material;

(i) decreasing the molecular weight of said material;

(j) increasing the surface area of said material (k) applying a stress to said material;

(l) adding at least one hydrophobic compound to said material;

(m) adding at least one end-capping agent to said material; and (n) cross-linking said material.

123. The method of claim 122, wherein said material is further degraded by biological degradation.

124. The method of claim 122, wherein said material is further degraded by microbial degradation.

125. The disposable material of claim 124, wherein said microbial degradation is augmented by adding at least one source of nutrients to said material.

126. The disposable material of claim 122, wherein said hydroxycarboxylic acid is an α-hydroxy-carboxylic acid.

127. The disposable material of claim 122, wherein said hydroxy carboxylic acid is selected from the group consisting of lactic acid, glycolic acid, tartaric acid, malic acid, mandelic acid, benzylic acid, hydroxyvaleric acid, 1-hydroxy-1-cyclohexane carboxylic acid, 2-hydroxy-2-(2-tetrahydrofuranyl) ethanoic acid, 2-hydroxy-2-(2-furanyl) ethanoic acid, 2-hydroxy-2-phenylpropionic acid, 2-hydroxy-2-methyl-propionic acid, 2-hydroxy-2-methylbutanoic acid, 2-hydroxy-2-ethylhexylcarboxylic acid, α-hydroxy-butyric acid, α-hydroxyisobutyric acid, α-hydroxy-pentanoic acid, α-hydroxyhexanoic acid, α-hydroxy-heptanoic acid, α-hydroxyctanoic acid, α-hydroxynon-anoic acid, α-hydroxydecanoic acid, α-hydroxy-dodecanoic acid, α-hydroxymyristic acid, α-hydroxy-palmitic acid, α-hydroxystearic acid, α-hydroxy-arachidic acid, α-hydroxybehenic acid, α-hydroxy-lignoceric acid, α-hydroxycerotic acid, α-hydroxy-oleic acid, α-hydroxylinoleic acid, α-hydroxylin-olenic acid, α-hydroxyarachidonic acid, α-hydroxy-pelargonic, α-hydroxyundecanoic acid, α-hydroxy-tridecanoic acid, α-hydroxypentadecanoic acid, α-hydroxyheptadecanoic acid, α-hydroxynonadecanoic acid, and mixtures thereof.

128. The disposable material of claim 122, wherein said hydroxycarboxylic acid is selected from the group consisting of lactic acid, glycolic acid, tartaric acid, malic acid, mandelic acid, benzylic acid, hydroxyvaleric acid, α-hydroxybutyric acid, α-hydroxyoctanoic acid, α-hydroxystearic acid, and mixtures thereof.

129. The disposable material of claim 122, wherein said hydroxy-carboxylic acid is selected from the group consisting of lactic acid, glycolic acid, and mixtures thereof.

130. The disposable material of claim 122, wherein said disposable material is selected from the group consisting of lactones, aliphatic esters of glycols, aliphatic esters of dicarboxylic acids; and mixtures thereof.

131. The disposable material of claim 122, wherein said disposable material comprises a polymer selected from the group consisting of polylactic acids, polylactides, polyglycolic acids, polyglycolides, substituted polyglycolic acids, substituted polyglycolides, caprolactone polymers, valerolactone polymers, and copolymers thereof.

132. The disposable material of claim 122, wherein said disposable material is selected from the group consisting of films, foams, coatings, molded articles, extruded articles, nonwoven fibers, pellets, powders, laminates, and adhesives.

133. The disposable material of claim 122, wherein said disposable material is selected from the group consisting of films, foams, coatings, and molded articles.

134. The disposable material of claim 122, wherein said disposable material comprises a packaging material.

135. The disposal material of claim 122, wherein said degradation rates comprise changes in the molecular weight of said disposable material over time.

136. The disposable material of claim 135, wherein said operative degradation rate is less than about 33 percent of said disposal degradation rate.

137. The disposable material of claim 135, wherein said operative degradation rate is less than about 10 percent of said disposal degradation rate.

138. The disposable material of claim 135, wherein said operative degradation rate is less than about 5 percent of said disposal degradation rate.

139. The disposable material of claim 122, wherein said material is capable of being about 100 percent hydrolytically degraded after discard.

140. The disposable material of claim 122, therein said material is at least about 98 percent hydrolytically degraded within about ten years after discard.

141. The disposable material of claim herein said material is at least about 98 percent hydrolytically degraded within about five years after discard.

142. The disposable material of claim 122, wherein said material is at least about 98 percent hydrolytically degraded within about three years after discard.

143. The disposable material of claim 122, wherein said disposable material is further biologically degraded to essentially carbon dioxide and water.

144. The disposable material of claim 122, wherein said disposable material is further biologically degraded to essentially carbon dioxide and methane.

145. An environmentally degradable disposable material comprising a hydroxycarboxylic acid-containing polymer, wherein said hydroxycarboxylic acid is selected from the group consisting of lactic acid, L-lactide, D-lactide, D,L-lactide, and mixtures thereof, wherein said material degrades hydrolytically during operative and disposal stages in a controlled manner such that the disposal degradation rate of said material is accelerated relative to the operative degradation rate of said material, and wherein said operative degradation rate is less than about 50 percent of said disposal degradation rate.

146. A disposable material of claim 145, wherein said material is a packaging material.

147. The disposal material of claim 145, wherein said degradation rates comprise changes in the molecular weight of said disposable material over time.

148. The disposable material of claim 147, wherein said operative degradation rate is less than about 33 percent of said disposal degradation rate.

149. The disposable material of claim 147, wherein said operative degradation rate is less than about 5 percent of said disposal degradation rate.

150. The disposable material of claim 145, wherein said material is at least about 98 percent hydrolytically degraded within about five years after discard.

151. A disposable material of claim 145, wherein said material further comprises at least one microencapsulated activator compound.

152. A disposable material of claim 151, said activator compound is selected from the group consisting of an acidic compound and a moisture-containing compound and wherein said disposable material is coated or laminated with said microencapsulated activator compound.

153. A disposable material of claim 145, rein said material further comprises at least one blotting compound.

154. A disposable material of claim 153, wherein said blotting compound is a water grabber.

155. A disposable material of claim 145, wherein said material further comprises an abrasion-prone, hydrophobic coating.

156. A disposable material of claim 155, wherein said abrasion-prone, hydrophobic coating has a contact angle of at least about 90 degrees.

157. A disposable material of claim 155, wherein said material further comprises a coating comprising at least one blotting compound positioned underneath said abrasion-prone, hydrophobic coating.

158. A disposable material of claim 145, further comprising a lactide-tetramethyl glycolide copolymer.

159. A disposable material of claim 145, further comprising a plasticizer selected from the group consisting of ketones or cyclic amides.

* * * * *